US012576134B2

(12) United States Patent
Ma et al.

(10) Patent No.: US 12,576,134 B2
(45) Date of Patent: Mar. 17, 2026

(54) ANTIVIRAL LECTIN AND USES THEREOF

(71) Applicant: ACADEMIA SINICA, Taipei City (TW)

(72) Inventors: Che Ma, New Taipei City (TW); Yo-Min Liu, Taipei City (TW); Jia-Tsrong Jan, Taipei City (TW)

(73) Assignee: ACADEMIA SINICA, Taipei City (TW)

( * ) Notice: Subject to any disclaimer, the term of this patent is extended or adjusted under 35 U.S.C. 154(b) by 998 days.

(21) Appl. No.: 17/274,122

(22) PCT Filed: Sep. 6, 2019

(86) PCT No.: PCT/US2019/049851
§ 371 (c)(1),
(2) Date: Mar. 5, 2021

(87) PCT Pub. No.: WO2020/051397
PCT Pub. Date: Mar. 12, 2020

(65) Prior Publication Data
US 2021/0386820 A1 Dec. 16, 2021

Related U.S. Application Data

(60) Provisional application No. 62/727,663, filed on Sep. 6, 2018.

(51) Int. Cl.
*A61P 31/16* (2006.01)
*A61K 38/17* (2006.01)

(52) U.S. Cl.
CPC ............ *A61K 38/178* (2013.01); *A61P 31/16* (2018.01)

(58) Field of Classification Search
CPC .... A61K 38/178; A61K 38/168; A61K 36/48; A61P 31/16; A61P 31/12; A61P 31/18; A61P 31/22; C07K 14/42
See application file for complete search history.

(56) References Cited

U.S. PATENT DOCUMENTS 4,742,046 A * 5/1988 Bliah ..................... C07K 14/42
530/370
2011/0085981 A1 4/2011 Wang

OTHER PUBLICATIONS

Bojar et al., A useful guide to lectin binding: machine-learning directed annotation of 57 unique lectin specificities; 2022, ACS Chem. Biol., 17: 2993-3012. (Year: 2022).*
Im et al., Dolichos lablab protects against nonalcoholic fatty liver disease in mice fed high-fat diets; J Med Food, 2017, 20 (12): 1222-1232. (Year: 2017).*
Hamelryck et al., "The Role of Weak Protein-Protein Interactions in Multivalent Lectin-Carbohydrate Binding: Crystal Structure of Cross-linked FRIL", Journal of Molecular Biology, Jun. 16, 2000, vol. 299, No. 4, pp. 875-883.
International Search Report for PCT/US2019/049851 (PCT/ISA/210) mailed on Dec. 4, 2019.
Kumar et al., "N-glycan analysis of mannose/glucose specific lectin from Dolichos lablab seeds", International Journal of Biological Macromolecules, Aug. 2014, Epub Jun. 4, 2014, vol. 69, pp. 400-407.
Written Opinion of the International Searching Authority for PCT/US2019/049851 (PCT/ISA/237) mailed on Dec. 4, 2019.

* cited by examiner

*Primary Examiner* — Daniel E Kolker
*Assistant Examiner* — James Ryland Melchior
(74) *Attorney, Agent, or Firm* — Birch, Stewart, Kolasch & Birch, LLP

(57) ABSTRACT

The present invention relates to antiviral lectin and uses thereof. Particularly, the present invention relates to a complex-type (CX-type) and/or hybrid-type (HY-type) glycan binding lectin for use in treating or preventing influenza virus infection. The present invention also provides a method for treating or preventing influenza virus infection by administrating to a subject in need said lectin or a composition comprising the same.

13 Claims, 16 Drawing Sheets

Specification includes a Sequence Listing.

| Lablab purpureus aqueous extract | → | sedimentation with ammonium sulfate | → | affinity chromatography with mannose-sepharose beads |

→ | anion exchange with Q column |

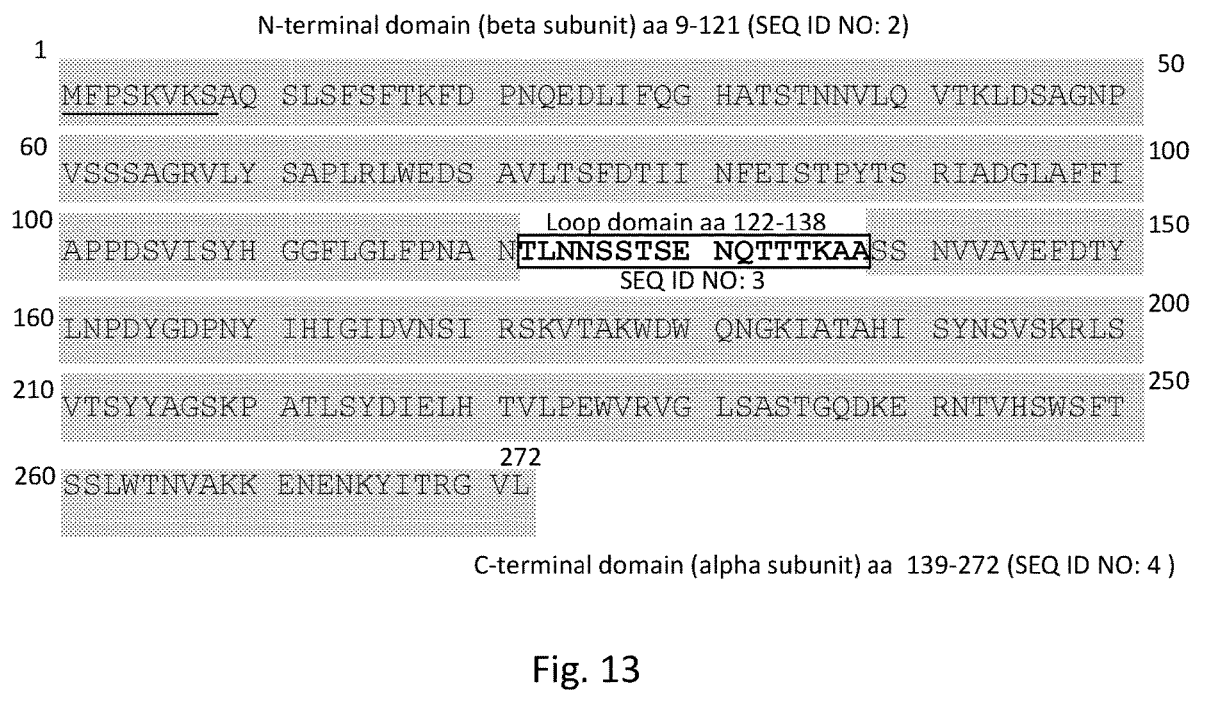

N-terminal domain (beta subunit) aa 9-121 (SEQ ID NO: 2)

1                                                                                          50

MFPSKVKSAQ  SLSFSFTKFD  PNQEDLIFQG  HATSTNNVLQ  VTKLDSAGNP 60                                                                                        100

VSSSAGRVLY  SAPLRLWEDS  AVLTSFDTII  NFEISTPYTS  RIADGLAFFI

100                                        Loop domain aa 122-138                         150

APPDSVISYH  GGFLGLFPNA  N TLNNSSTSE  NQTTTKAA SS  NVVAVEFDTY
                                            SEQ ID NO: 3

160                                                                                       200

LNPDYGDPNY  IHIGIDVNSI  RSKVTAKWDW  QNGKIATAHI  SYNSVSKRLS 210                                                                                       250

VTSYYAGSKP  ATLSYDIELH  TVLPEWVRVG  LSASTGQDKE  RNTVHSWSFT

272

260 SSLWTNVAKK  ENENKYITRG  VL

C-terminal domain (alpha subunit) aa  139-272 (SEQ ID NO: 4 )

Fig. 13

ANTIVIRAL LECTIN AND USES THEREOF

RELATED APPLICATIONS

This application claims the benefit of U.S. provisional application No. 62/727,663, filed Sep. 6, 2018 under 35 U.S.C. § 119, the entire content of which is incorporated herein by reference.

BACKGROUND OF THE INVENTION

The influenza pandemic is a major threat to human health, and highly aggressive strains such as H1N1, H5N1, H3N2 and H7N9 have emphasized the need for therapeutic strategies to combat these pathogens. Influenza antiviral agents play important roles in controlling pandemics while vaccines are developed. Currently, two classes of antiviral agents, which function as influenza neuraminidase (NA) inhibitors and M2 ion channel protein inhibitors, are approved in clinical. Among two classes of FDA-approved antiviral drugs, neuraminidase (NA) inhibitors, oseltamivir, zanamivir, and peramivir, are currently the only choice for the prevention and treatment of influenza virus infection.

This rapid mutation capability of the influenza virus is particularly exacerbated in the context of the growing threat from the present H1N1 swine flu pandemic as well as the alarming worldwide spate in recent infections with highly pathogenic avian H5N1 'bird flu' influenza strains. (Khanna et al., Journal of Biosciences, 33(4):475, 2008, Soundararajan et al., Nature Biotechnology 27:510, 2009). Furthermore, two of the major flu pandemics of the last century originated from avian flu viruses that changed their genetic makeup to allow for human infection.

There is a need for the development of effective anti-influenza prophylactics and therapeutics. Furthermore, given the high degree of unpredictability in evolution of these influenza viruses, there is a particular need for the development of cross-strain effective (e.g., "universal" or "broad spectrum") anti-influenza prophylactics and therapeutics. Such effective anti-influenza agents, and particularly such universal or broad spectrum anti-influenza agents could replace or augment vaccines designed to target specific seasonal viral strains in circulation (Ekiert et al., Science, 324(5924):246, 2009 and Sui et al., Nat Struct Mol Biol. 16(3):265, 2009). Alternatively or additionally, there is a need for the development of effective anti-influenza prophylactics or therapeutics that can replace or augment current anti-viral therapy.

SUMMARY OF THE INVENTION

The present invention is based on the unexpected findings that a complex-type (CX-type) and/or hybrid-type (HY-type) glycan binding lectin (a CX/HY-type binding lectin) exhibits broad-spectrum antiviral activity against multiple influenza virus strains. This is the first report that such lectin displays antiviral activity that can effectively neutralize multiple influenza virus strains. These findings indicate that a CX/HY-type binding lectin can serve as a broad-spectrum neutralization agent against various influenza viruses.

Accordingly, the present invention provides a method for treating or preventing influenza virus infection, the method comprising administering to a subject in need thereof an effective amount of a CX/HY-type binding lectin or a composition comprising the same.

Particularly, a CX/HY-type binding lectin as described herein is capable of specifically binds to a CX-type glycan and/or a HY-type glycan on influenza virus which contain a trimannosyl core and at least one N-acetylglucosamine (GlcNAc) attached to the 1,3 mannose arm and/or the 1,6 mannose arm of the trimannosyl core and one or more antenna residues (e.g., galactose, fucose and sialic acid). In certain embodiments, the CX/HY-type glycan has a α 1-3 linked Manβ1-2GlcNAcβ1-4(Fucα1-3)Gal moiety and/or α 1-6 linked Manβ1-2GlcNAcβ1-4(Fucα1-3)Gal moiety. Specifically, the CX/HY-type binding lectin as used herein is not a high mannose-type binding lectin (a HM-type binding lectin).

In some embodiments, a CX/HY-type binding lectin as described herein is in a form of a multimer e.g. a dimer, trimer or tetramer.

In some embodiments, a CX/HY-type binding lectin as described herein is an Flt3 receptor interacting lectin (FRIL) protein from Lablab purpureous. In some embodiments, the FRIL protein is a native FRIL purified from an extract of Lablab purpureus. In some embodiments, the FRIL protein is a native FRIL purified from an aqueous extract of Lablab purpureus. In some embodiments, the FRIL protein can be recombinant which can be overexpressed from bacteria, yeast, insect cells, baculovirus, mammalian cells, or human cells. In certain embodiments, the FRIL protein comprises an amino acid sequence of SEQ ID No: 1, or an amino acid sequence that is substantially identical to SEQ ID NO:1. In certain embodiments, the FRIL protein comprises a FRIL polypeptide in a cleaved form (removal of a loop domain). Specifically, a cleaved form of FRIL includes a N-terminal domain (beta subunit, e.g. SEQ ID NO: 2) and a C-terminal domain (alpha subunit, e.g. SEQ ID NO: 3). In some embodiments, the beta subunit and the alpha subunit are associated to form a monomer; further, two units of such monomer may be associated to form a dimer and two units of dimer may be associated to form a tetramer.

The subject described herein is suffering from or susceptible to influenza virus infection, or suspected of being infected to an influenza virus. The subject may be a human or non-human organism.

The lectin described herein may be formulated for administration by a route selected from the group consisting of oral, intravenous, intramuscular, intra-arterial, subcutaneous, intraventricular, transdermal, interdermal, rectal, intravaginal, intraperitoneal, topical, mucosal, nasal, buccal, enteral, sublingual, intratracheal and bronchial. In certain embodiments, the administration is by intratracheal and bronchial instillation. In certain embodiments, the administration may be by oral or nasal inhalation. In certain embodiments, the polypeptide described herein is formulated as an oral spray, a nasal spray, or an aerosol.

In yet another aspect, the present invention provides a pharmaceutical composition, comprising a lectin as described herein, and a pharmaceutically acceptable excipient. The provided pharmaceutical composition is useful for treating or preventing an influenza viral infection. The pharmaceutical composition may also optionally be included in a device for administration of the pharmaceutical composition, for example, by oral or nasal inhalation.

In some embodiments, the present invention provides a kit comprising a lectin as described herein e.g. a Lablab purpureus FRIL, formulated for administration via an administration device, together with such an administration device in a set comprising one or more containers. In some embodiments, an appropriate administration device is selected from the group consisting of a syringe, needle, spray, filter, applicator, and combinations thereof. In some embodiments, a provided kit includes instructions for use.

Provided lectin, compositions and methods are useful, for example, in research and/or in medicine. In some embodiments, provided proteins/polypeptides and methods are useful, for example, in prophylaxis, treatment, and/or study of influenza.

Furthermore, the present invention discloses that a lectin as described herein as an antiviral agent against other enveloped viruses. In addition to influenza virus, examples of well-known enveloped viruses include herpes virus, paramyxovirus, respiratory syncytial virus, corona virus, human immunodeficiency virus (HIV), hepatitis B virus, hepatitis C virus and SARS-CoV virus. In particular, a lectin as described herein as an antiviral agent is administered to a subject in need in an amount effective in neutralizing these enveloped viruses by binding to a CX-type and/or HY-type glycan on the envelope of the virus particles.

The details of certain embodiments of the invention are set forth herein. Other features, objects, and advantages of the invention will be apparent from the Detailed Description, the Figures, the Examples, and the Claims.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

4

Figure 6:
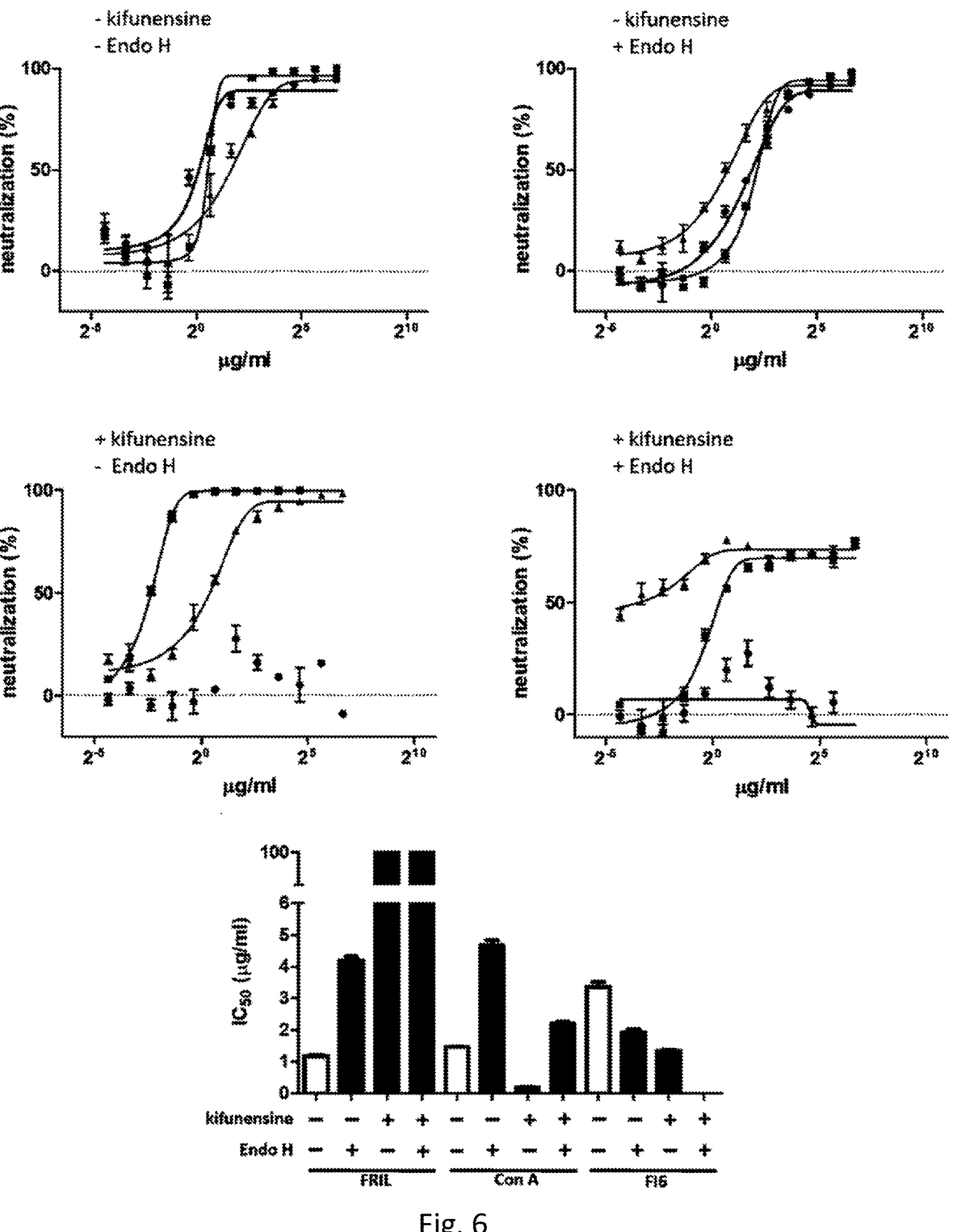

FIG. 6 shows that FRIL has a different neutralization mechanism than ConA. Microneutralization assay of FRIL (-●-), Con A (-■-) and bnab FI6v3 (-▲-) against kifunensine (a glycoprotein processing inhibitor) and Endo H-treated A/California/7/2009-like (H1N1) SDG-purified virus particles. Comparison of absolute $IC_{50}$s of FRIL (blue), ConA (green) and FI6 (orange) against different kifunensine and Endo H-treated A/California/7/2009-like (H1N1) SDG-purified virus particles. The $IC_{50}$ of FRIL (+KIF–EndoH) and (+KIF+EndoH) is above the range of our tested concentrations (>100 μg/ml), while FI6 (+KIF+EndoH) is below range (<50 ng/ml).

Figure 7:
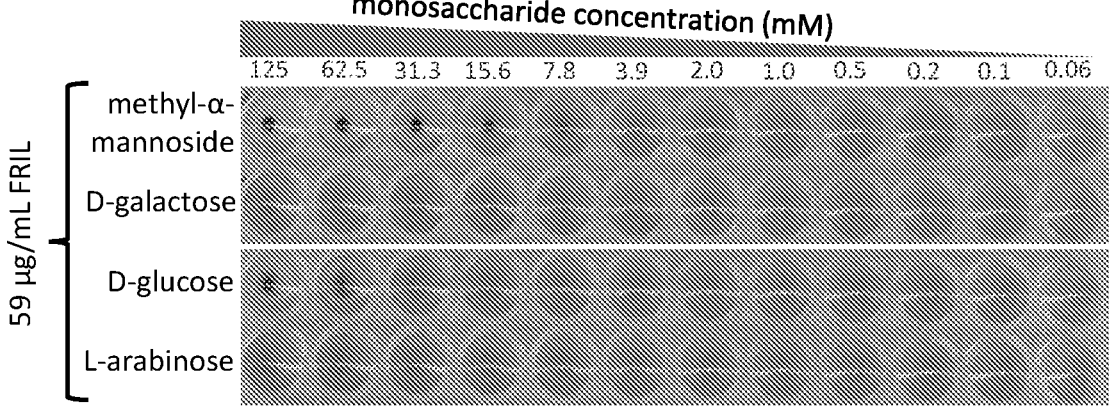
Figure 7:
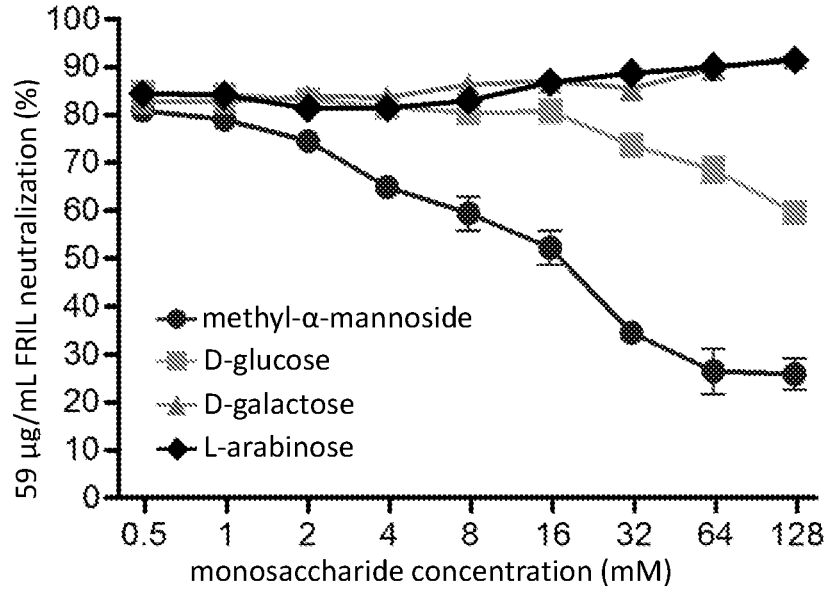

FIG. 7 shows inhibition of FRIL neutralization by disrupting sugar binding. Hemagglutination inhibition assay of α-mannoside, D-galactose, D-glucose and L-arabinose against FRIL. 4 HAUs of FRIL is ameliorated by 125~7.8 mM α-mannoside, or 125~62.5 mM D-glucose. FRIL microneutralization in the presence of inhibitory or noninhibitory monosaccharides. FRIL neutralization is only disrupted by monosaccharides that inhibit its lectin activity.

Figure 8:
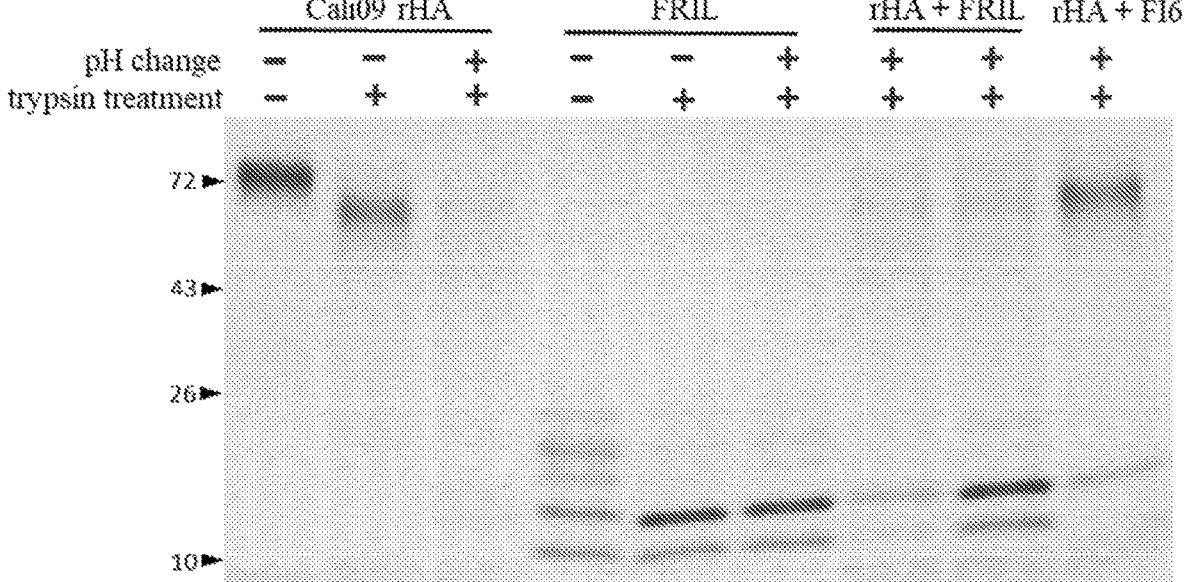

FIG. 8 shows trypsin susceptibility test. To measure recombinant HA conformational change inhibition, nonreducing, with a 4~15% SDS PAGE. Recombinant HA (rHA) remained susceptible to trypsin digestion after pH change when FRIL was added in a 1:1 (lane 7) or 1:3 ratio (lane 8), in contrast to a 1:1 ratio of known fusion inhibitor FI6 (lane 9). TPCK trypsin was added at a 1:50 ratio.

Figure 9A:
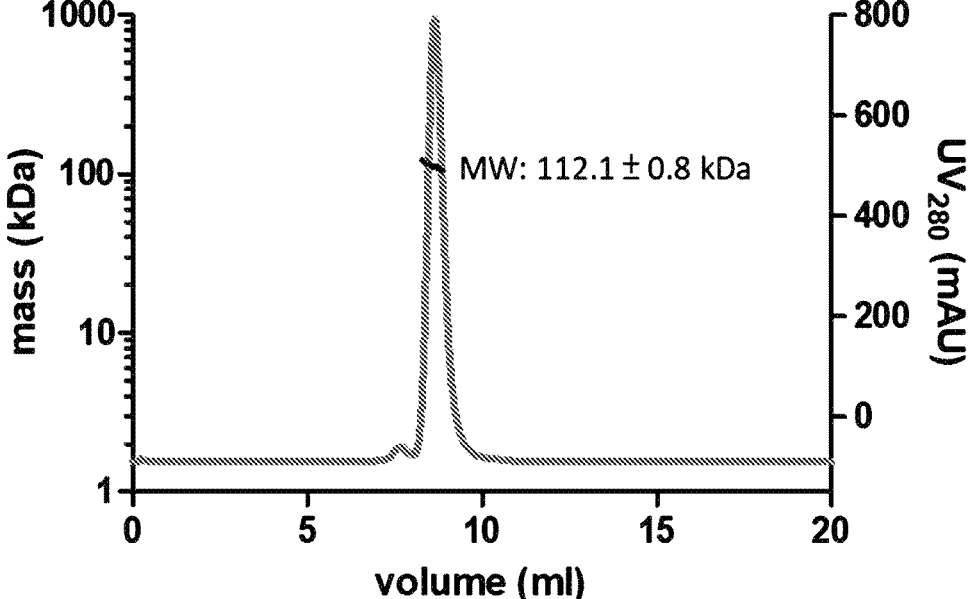

FIG. 9A shows determination of FRIL stoichiometry by SEC-MALS and negative stain electron microscopy. SEC-MALS analysis indicate that our purified FRIL forms a 112.2 kDa tetramer in solution (FRIL monomer is approximately 28 kDa).

Figure 9B:
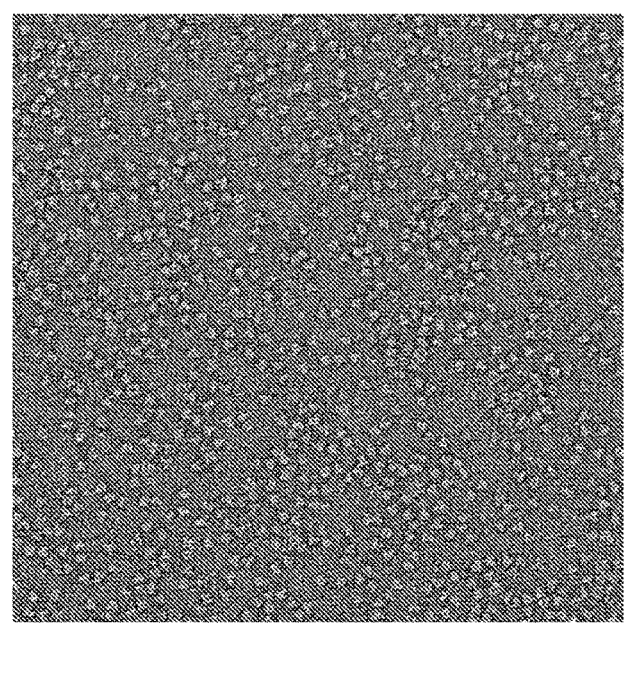
Figure 9B:
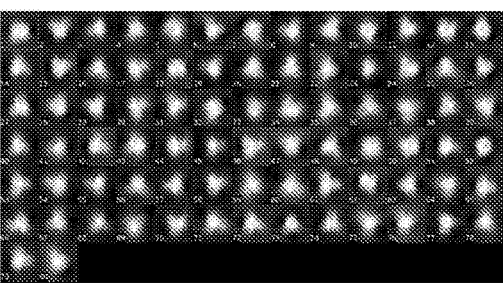
Figure 9B:
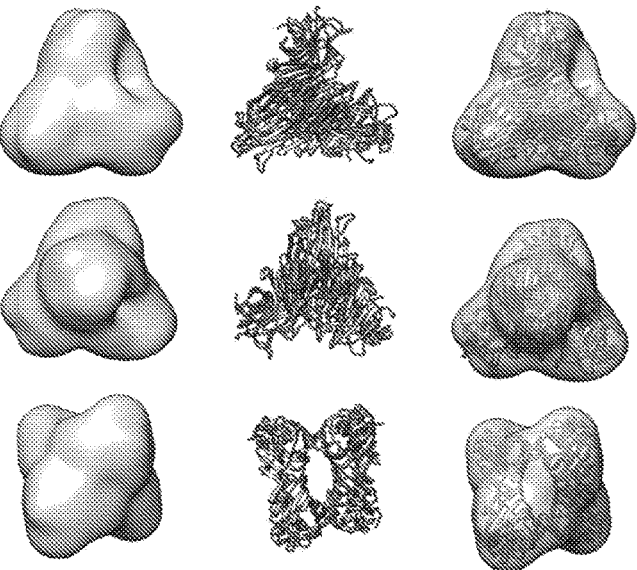

FIG. 9B shows determination of FRIL structure by negative stain electron microscopy. In negative staining EM (0.5% uranyl formate), 67,041 particles were chosen to reconstruct a 3D map, the resolution is 12.22 Å. A tetrameric structure is observed.

Figure 10A:
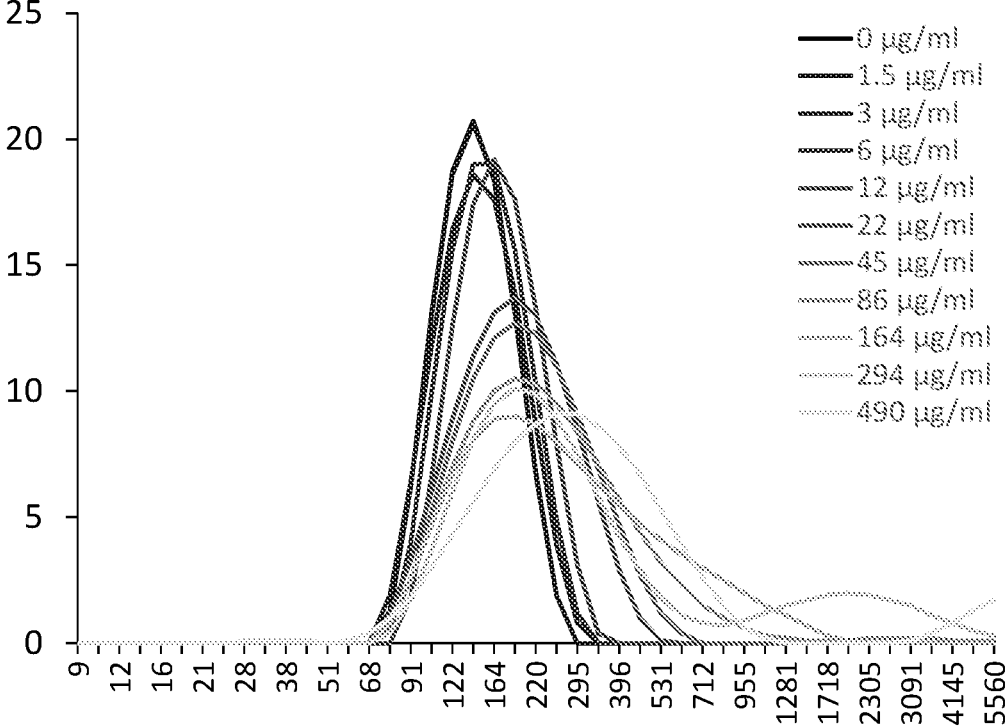

FIG. 10A shows aggregation of virus particles by FRIL by DLS. Dynamic light scattering measurement of FRIL aggregation of A/California/7/2009-like (H1N1) SDG-purified virus particles: no treatment (blue), no kifunensine+endoH (green), +kifunensine no endoH (orange) and +kifunensine+endoH (purple). (B) SDS PAGE of precipitant when recombinant A/California/7/2009 (H1N1) HA and FRIL are mixed in a 1:3 molar ratio.

Figure 10B:
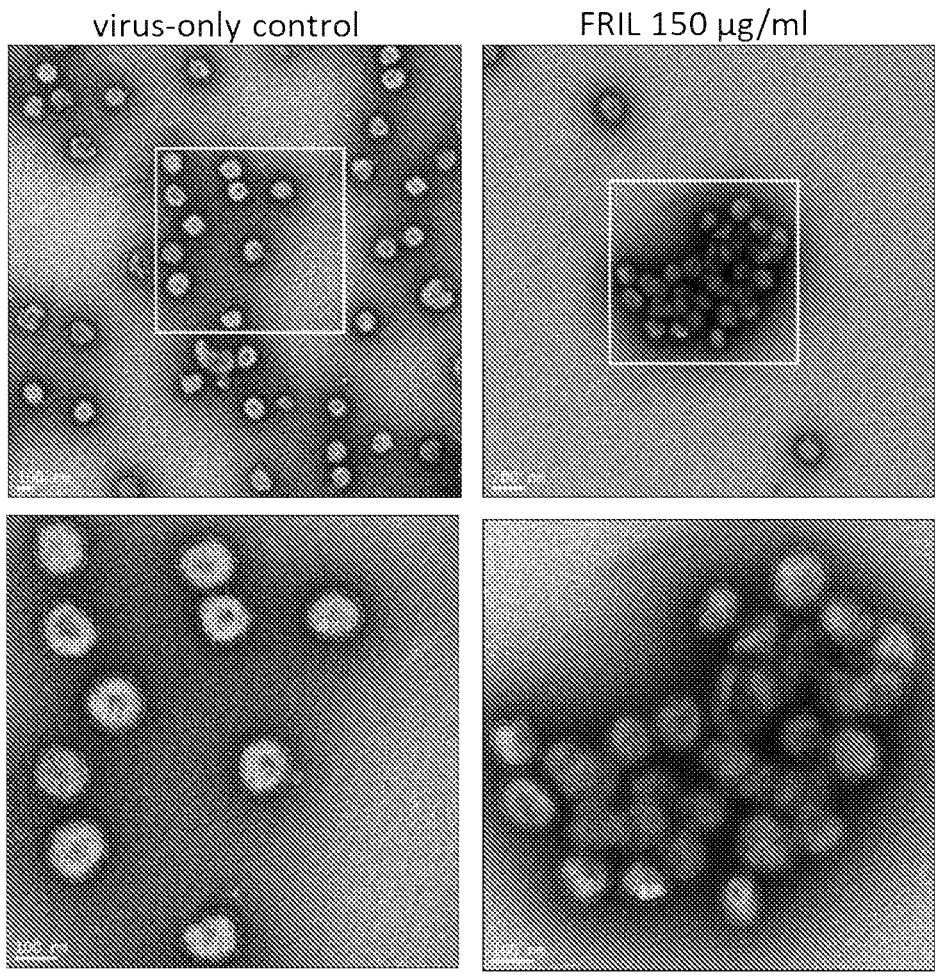

FIG. 10B shows aggregation of virus particles by FRIL under negative stain electron microscopy. Large three-dimensional aggregations of overlapping A/California/7/2009-like (H1N1) particles were observed at 150 μg/ml FRIL concentration, while little aggregation was seen for virus particles that were not treated with FRIL. Quantification of aggregation was done by manually counting virus particles in close proximity to one another (Table 2). We observed a dose-dependent increase in the percentage of aggregates up to 32 μg/ml FRIL, though concentrations higher than that formed densely-packed clumps of layered viruses that make it difficult to differentiate individual particles visually.

Figure 11:
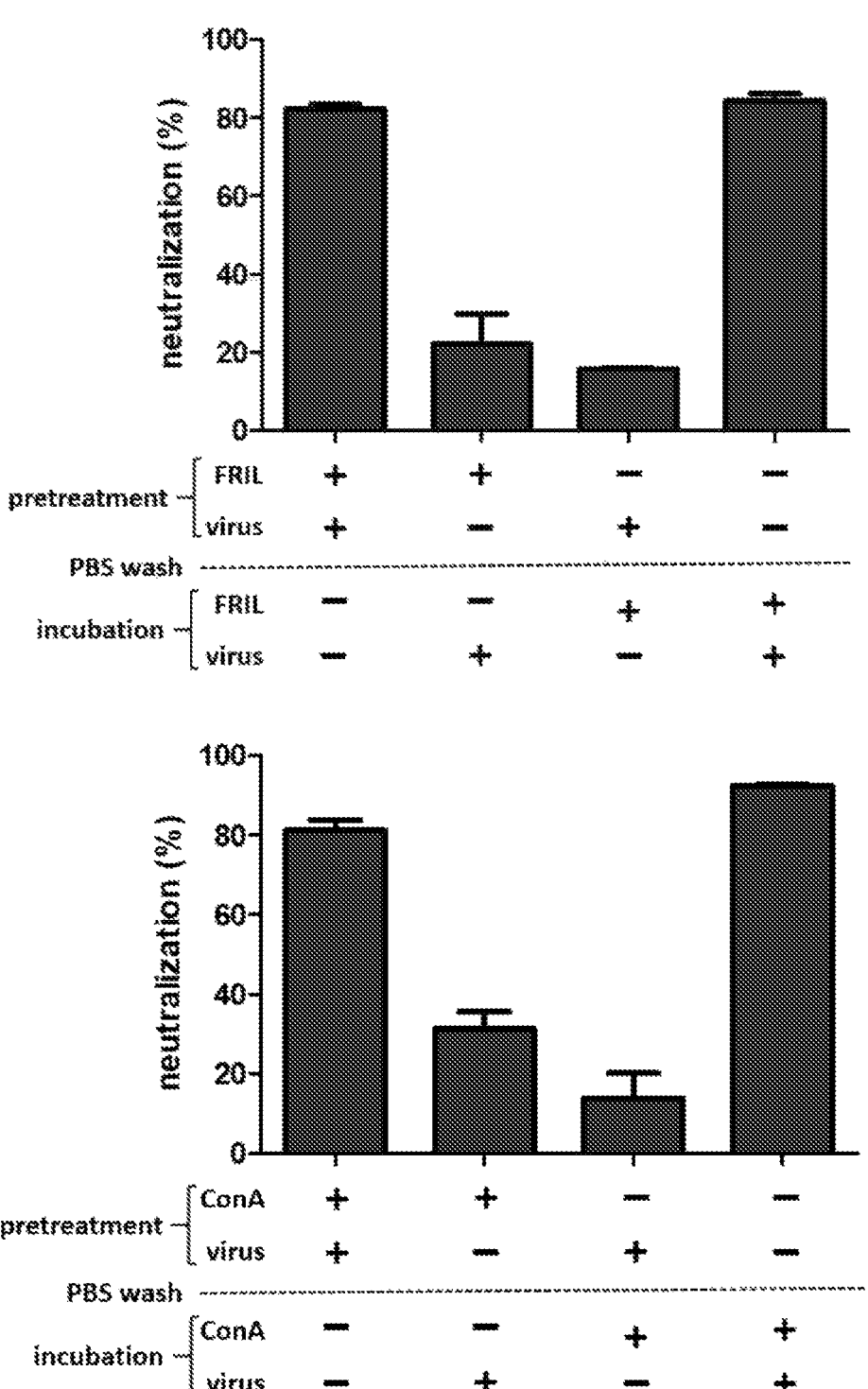

FIG. 11 shows microneutralization assay with pretreatment step. MDCK cells were either pre-treated with the lectin and the virus together (++), lectin only (+–), virus only (–+) or culture medium (– –). After washing (PBS wash) the pretreatment solution off, the cells are then incubated with culture medium (– –), virus only (–+), lectin only (+–) and lectin and the virus together (++) respectively. (Upper panel) Pretreatment assay with FRIL. (lower panel) Pretreatment assay with ConA.

Figure 12:
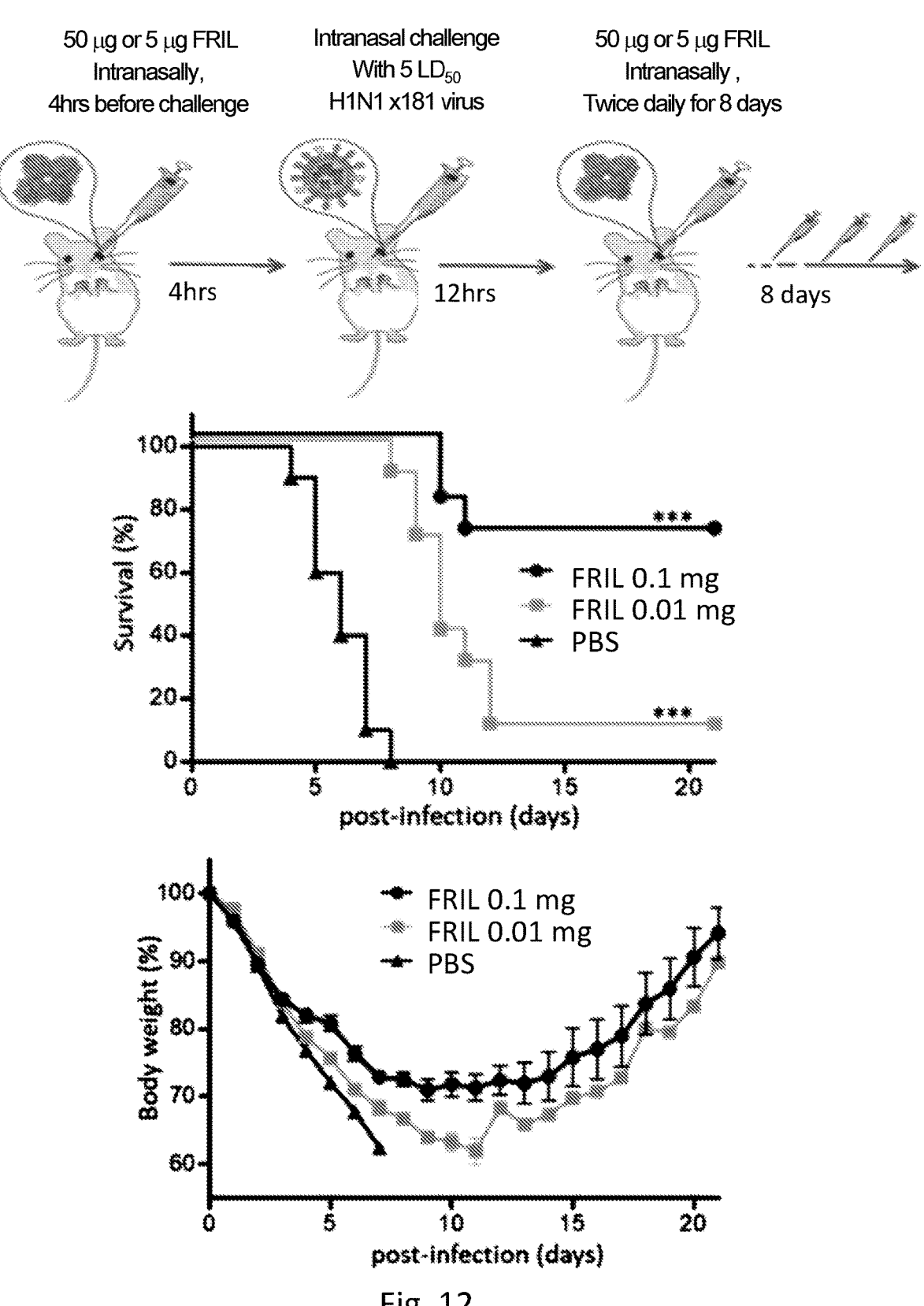

FIG. 12 shows that intranasal administration procedures of FRIL and the results, indicating that FRIL protects mice from a lethal dose of H1N1 X-181 influenza virus challenge and the body weight, without FIG. 13 shows sequence features of FRIL as used herein in some embodiments of the present invention.

DETAILED DESCRIPTION OF THE INVENTION

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the singular forms "a", "an", and "the" include plural referents unless the context clearly dictates otherwise. Thus, for example, reference to "a component" includes a plurality of such components and equivalents thereof known to those skilled in the art.

As used herein, the term "comprise" or "comprising" is generally used in the sense of include/including which means permitting the presence of one or more features, ingredients or components. The term "comprise" or "comprising" encompasses the term "consists" or "consisting of."

As used herein, the term "polypeptide" refers to a polymer composed of amino acid residues linked via peptide bonds, for example, composed of 1,000 amino acids or less, e.g. 800 or less, 600 or less, 400 or less, 300 or less, 150 or less, 100 or less, 50 or less, 25 or less, 20 or less amino acids in length. In some embodiments, the terms "polypeptide" and "proteins" are used interchangeably herein. In some embodiment, a polypeptide as described herein may be meant to include native, synthesized, recombinant, and/or degraded or digested forms.

As used herein, "corresponding to," refers to a residue at the enumerated position in a protein or peptide, or a residue that is analogous, homologous, or equivalent to an enumerated residue in a protein or peptide.

As used herein, the term "substantially identical" refers to two sequences having more than 85%, preferably 90%, more preferably 95%, and most preferably 100% homology.

To determine the percent identity of two sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

It is understandable that a polypeptide may have a limited number of changes or modifications that may be made within a certain portion of the polypeptide irrelevant to its activity or function and still result in a variant with an acceptable level of equivalent or similar biological activity or function. The term "acceptable level" can mean at least 20%, 50%, 60%, 70%, 80%, or 90% of the level of the referenced protein as tested in a standard assay as known in the art. Biologically functional variant polypeptides are thus defined herein as those polypeptides in which certain amino acid residues may be substituted. Polypeptides with different substitutions may be made and used in accordance with the invention. Modifications and changes may be made in the structure of such polypeptides and still obtain a molecule having similar or desirable characteristics. For example, certain amino acids may be substituted for other amino acids in the peptide/polypeptide structure without appreciable loss of activity. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989. For example, conservative substitutions of amino acids include substitutions made amongst amino acids within the following groups: (i) A, G; (ii) S, T; (iii) Q, N; (iv) E, D; (v) M, I, L, V; (vi) F, Y, W; and (vii) K, R, H.

The polypeptide of the present invention may be produced by chemical synthesis using techniques well known in the chemistry of proteins such as solid phase synthesis or synthesis in homogenous solution. The polypeptide of the present invention may also be obtained from natural source and isolated by extraction. See FIGS. 1 and 2, for example.

In some embodiments, the polypeptide of the present invention may be prepared using recombinant techniques. In this regard, a recombinant nucleic acid comprising a nucleotide sequence encoding a polypeptide of the present invention and host cells comprising such recombinant nucleic acid are provided. The host cells may be cultured under suitable conditions for expression of the polypeptide of interest. In certain embodiments, the host cell may be bacterial, fungal, insect or mammalian. In eukaryotic expression systems, it will be appreciated by persons skilled in the art that the polypeptides of the invention may undergo post-translation modification by the host cells e.g. glycosylation, phosphorylation. Expression of the polypeptides may be constitutive such that they are continually produced or inducible, requiring a stimulus to initiate expression. In the case of inducible expression, protein production can be initiated when desired by, for example, addition of an inducer substance to the culture medium, for example, isopropyl β-D-1-thiogalactopyranoside (IPTG) or methanol. Polypeptide can be recovered and purified from host cells by a number of techniques known in the art, for example, chromatography e.g., HPLC or affinity columns.

In some embodiments, the polypeptide of the present invention can be said to be "isolated" or "purified" if it is substantially free of cellular material or chemical precursors or other chemicals that may be involved in the process of polypeptide preparation or extraction. It is understood that the term "isolated" or "purified" does not necessarily reflect the extent to which the polypeptide has been "absolutely" isolated or purified e.g. by removing all other substance s (e.g., impurities or cellular components). In some cases, for example, an isolated or purified polypeptide includes a preparation containing the peptide having less than 50%, 40%, 30%, 20% or 10% (by weight) of other proteins (e.g. cellular proteins), having less than 50%, 40%, 30%, 20% or 10% (by volume) of culture medium, or having less than 50%, 40%, 30%, 20% or 10% (by weight) of chemical precursors or other chemicals involved in synthesis procedures.

Influenza virus is an enveloped RNA virus of the Othromyxovirus family. There are three types of influenza virus: A, B, and C. The two genres responsible for major seasonal and pandemic flu infections in humans, influenza A and B, have two glycoproteins on their viral envelope: hemagglutinin (HA) and neuraminidase (NA). The N-glycosylation of these two membrane proteins can contain a variety of complex, high-mannose, or hybrid type oligosaccharides, many of which are essential for protein structure or evasion from host antibody detection [1, 2].

The addition of more glycosylation sites, especially on the HA, to mask neutralizing epitopes is thought to be a major contributor to antigenic drift and sustained circulation of the virus in a population with increasing immunity. However, this strategy also comes with significant costs to viral fitness, as too many glycosylation sites near its receptor binding site could affect HA receptor binding avidity, as well as rendering it susceptible to collectins of the innate immune system [2]. As it currently stands, many circulating influenza subtypes have steadily increased the number of glycosylation sites on their HA since their initial introduction [3].

The terms "influenza A subtype" or "influenza A virus subtype" are used interchangeably, and refer to influenza A virus variants that are characterized by a hemagglutinin (H) viral surface protein, and thus are labeled by an H number, such as, for example, H1, H3, and H5. In addition, the subtypes may be further characterized by a neuraminidase (N) viral surface protein, indicated by an N number, such as, for example, N1 and N2. As such, a subtype may be referred to by both H and N numbers, such as, for example, H1N1, H5N1, and H5N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably. Subtypes contain antigens based upon an influenza A virus. The antigens may be based upon a hemagglutinin viral surface protein and can be designated as "HA antigen". In some instances, such antigens are based on the protein of a particular subtype, such as, for example, an H1 subtype and an H5 subtype, which may be designated an H1 antigen and an H5 antigen, respectively.

As used herein, the term "N-glycan" means an N-linked polysaccharide or oligosaccharide. For example, an N-linked oligosaccharide is one that is attached by an N-acetylglucosamine residue linked to the amide nitrogen of an asparagine residue in a protein. N-glycans have a common pentasaccharide core structure of $Man_3GlcNAc_2$ (Man3) (Man=mannose; Glc=glucose; Nac=N-acetyl; GlcNAc=N-acetylglucosamine). N-glycans are classified with respect to their branched (antennae) constituents that are added to the $Man_3GlcNAc_2$ core structure (e.g., high mannose, complex or hybrid). A "high mannose type" (HM-type) N-glycan typically means an N-linked polysaccharide or oligosaccharide having only mannose in the antennae, for example, having totally five mannose residues (Man5), or more mannose residues (e.g. Man6, Man7, Man8, Man9). A "complex-type" (CX-type) N-glycan typically means N-linked polysaccharide or oligosaccharide which has at least one GlcNAc attached to the 1,3 mannose arm and at least one GlcNAc attached to the 1,6 mannose arm of a "trimannose" core. A "hybrid type" (H-type) N-glycan means a N-linked polysaccharide or oligosaccharide which has at least one GlcNAc on the terminal of the 1,3 mannose arm of the trimannose core and zero or more mannoses on the 1,6 mannose arm of the trimannose core. The GlcNAc attached to the 1,3 mannose arm and/or the 1,6 mannose arm may further have additional antennae residues, particularly galactose (Gal), sialic acid (SA) and fucose (Fuc) residues. In certain embodiments, a CX-type and/or a HY-type glycan has a α 1-3 linked Manβ1-2GlcNAcβ1-4 (Fucα1-3)Gal moiety and/or α 1-6 linked Manβ1-2GlcNAcβ1-4(Fucα1-3)Gal moiety.

Lectins are carbohydrate-binding proteins found in diverse phyla throughout nature. Legume lectins are a historically well-characterized family of lectins, exemplified by Concanavalin A (ConA) from the jackbean *Concanvalia ensiformis*. This large family represents over 50 lectins and two non-lectins in diverse legume species, sharing a conserved tertiary structure and sequence identity (>35%) throughout [9]. Even though they share a similar structure, their carbohydrate specificity, determined by a monosaccharide specificity loop surrounded by a limited number of variable residues, is far from monolithic. Studies have found lectins that are Glc/Man specific (ConA, Vicieae lectins), Gal/Galnac specific (peanut agglutinin), fucose specific (UEA-1 from *Ulex europaeus*), and complex specificity (Lewis-b tetrasaccharide specificity found in lectin IV from *Griffonia simplicifolia*) [9, 10]. Furthermore, the propensity of this family of lectins to form quaternary structures such as dimer and tetramers allow them to exert a number of interesting biological effects.

Increasingly over the past decade, lectins such as cyanovirin-N, scytovirin and griffithsin have been reported to display antiviral activity against numerous enveloped viruses. Lectins are carbohydrate-binding proteins found in diverse phyla throughout nature. Research into the discovery, the spectrum of antiviral activity, the specific mechanism by which lectins bind their target oligosaccharides on envelope glycoproteins, the structural basis of lectin carbohydrate specificity, the mechanism of lectin antiviral activity and its dependence on both affinity and avidity and the avenues by which viruses can become resistant to lectins, have been pursued by numerous research groups. Despite the promising prospect of using plant lectins as antivirals, considerable hurdles still need to be overcome before these agents can be utilized clinically. The introduction of a foreign agent into the human body, their hemagglutination/leucoagglutination ability [25], and their mitogenic effect [26] are major concerns. Also, ConA induces hepatoxicity by binding to sinusoidal endothelial cells [27], a trait that may be shared by its close relatives in the legume lectin family. The only antiviral lectin that is currently in clinical trials is Griffithsin (GRFT), a mannose-binding lectin isolated from the red algae *Griffithsia* sp. as a vaginal gel for the prevention of HIV [28]. The in vivo efficacy of lectins for antiviral therapy and prophylaxis is also an area of continuing research including all aspects of their toxicity, immunogenicity and their large-scale production for clinical utility.

As used herein, the term "a complex-type (CX-type) glycan binding lectin" refers to a lectin that can specifically binds to a complex-type N-glycan.

As used herein, the term "a hybrid-type (HY-type) glycan binding lectin" refers to a lectin that can specifically binds to a hybrid-type N-glycan.

As used herein, the term "a high mannose-type (HM-type) glycan binding lectin" refers to a lectin that hat can specifically binds to a high mannose-type N-glycan.

As used herein, a molecule is said to exhibit "specific binding" if it reacts or associates more frequently, more rapidly, with greater duration and/or with greater affinity with a particular target than it does with alternative targets. It is also understood by reading this definition that, for example, a lectin molecule that specifically binds to a first carbohydrate target may or may not specifically or preferentially bind to a second carbohydrate antigen. As such, "specific binding" or "preferential binding" does not necessarily require (although it can include) exclusive binding. Generally, but not necessarily, reference to binding means preferential binding.

*Lablab purpureus*, previously known as *Dolichos lablab* and commonly called the hyacinth bean, field bean or Indian *Lablab* bean, is a legume in the Fabaceae family. It is grown as an ornamental garden plant, homegarden plant or cattle feed around the world [30], and is also reported to have medicinal properties in Chinese traditional medicine (CTM). Two lectins have been isolated from the aqueous extract of the *Lablab purpureus* seed [11, 12]: *Dolichos lablab* lectin 1 (DLL1) a purported Glc/Man lectin [13], and *Dolichos lablab* lectin 2 (DLL2) a galactose specific lectin with polyphenol oxidase activity [14, 15]. DLL1 is also known as Flt3 Receptor Interacting Lectin (FRIL) for its ability to prolong hematopoietic progenitor cells in suspension culture [16]. See also PCT/US2006/013149 (WO 2006/110577).

The cDNA sequence and crystal structure of FRIL has previously been elucidated [16, 17]. The cDNA sequence shows a FRIL monomer is translated as one single peptide (pro-lectin), then post-translationally processed into α- and β-subunits by proteolytic digestion of its connecting loop and c-terminus in the vacuole. The cDNA sequence also shows a 48% sequence identity with ConA. The structure of FRIL in complex with a Man(α1-3)[Man(α1-6)]Man trisaccharide resembles a typical ConA-like lectin [9] involving three β sheets: a 6-stranded back sheet, a 7-stranded front sheet, and a 2-stranded connecting sheet forming a scaffold on which a single carbohydrate recognition domain (CRD) is situated. Further studies have shown the proteolytic digestion of α- and β-subunit is not homogenous, and may or may not include two n-glycosylation sites at the start of the α-subunit (closest to the connecting loop), resulting in differences in molecular mass on an SDS PAGE [18]. There is no domain-swapping in FRIL multimers.

The carbohydrate specificity of FRIL has been previously determined by hemagglutination inhibition assay (HAI) and an ELISA-based detection of inhibition of FRIL binding to solid-phase bound IgM [13]. The best monosaccharide ligands were reported to be mannose, glucose, and N-acetylglucosamine, with a strong preference for the α-anomeric configuration. Among oligosaccharides, trehalose, trehalosamine and the branched trimannoside Man(α1-3)[Man(α1-6)]ManOMe were reported to be the best ligands. Structurally different yeast mannans all failed to precipitate the lectin. An old study comparing FRIL and ConA by their immunoprecipitation profiles on solubilized mouse splenocyte membrane protein showed they bind to different proteins, despite the similarity of their monosaccharide affinity [19]. However, no study has been done on FRIL's binding affinity with N- or O-glycans commonly occurring on cell or viral glycoproteins.

Aside from the aforementioned Flt3 receptor interaction that helps preserve human cord blood progenitors, FRIL has also been shown to have potent mitogenic ability and elicitation of IL-2 secretion in T lymphocytes [20], preservation of neural progenitor cells, and exert anti-tumor activity by reducing neoangiogenesis through immunomodulation.

As far as we are aware there has been no mention in previous literature on FRIL having anti-viral or anti-influenza effects, although its close relative ConA's anti-influenza activity has been previously noted in passing [22].

According to the present invention, it is firstly demonstrated that FRIL is a CX/HY-type binding lectin exhibiting broad-spectrum antiviral activity against multiple influenza virus strains.

As used herein, the term "native FRIL" means a FRIL protein isolated from the seeds of *Lablab purpureous* in which the protein is naturally expressed.

As used herein, the term "recombinant FRIL" means a FRIL protein isolated from an organism in which the protein is expressed by a recombinant gene including, without limitation, bacteria, yeast, plant, or animal cells which have been transfected with a recombinant construct encoding the FRIL protein. A recombinant FRIL protein can have an amino acid sequence identical to a native FRIL protein, or a functional equivalent that can have an amino acid sequence including silent mutations e.g. one or more amino acid insertions, deletions, and/or substitutions including, without limitation, N-terminal additions or deletions, C-terminal additions or deletions, and chimeric proteins, without substantially changing its function.

As used herein, the term "FRIL" may refer to a native FRIL protein or a recombinant FRIL protein. In certain embodiments, FRIL is a protein including about 272 amino acids. It begins with a leading sequence of 8 amino acid residues in length at the N-terminal that is normally cleaved from a mature protein. Residues 9 to appropriately 121-138 constitute an N-terminal domain (beta subunit, about 12-18 kDa) and the residues from appropriately 122-139 to 272 constitute a C-terminal domain (alpha subunit, about 12-18 kDa), wherein the residues from about 122-138 constitutes a loop domain that is proteolytic digested in various degree (completely or partially). The exemplified amino acid sequence of FRIL is shown in FIG. 14 (SEQ ID NO: 1). In certain embodiment, the amino acid residues 9-121 (SEQ ID NO: 2) constitutes the N-terminal domain (beta subunit) and the amino acid residues 139-272 (SEQ ID NO: 4) constitutes the C-terminal domain (alpha subunit), linked by loop a loop domain of amino acid residues 122-138 (SEQ ID NO: 3). In certain embodiments, the beta subunit and the alpha subunit are associated to form a monomer (αβ). In certain embodiments, two units of such monomer may be associated to form a dimer (α2β2). In certain embodiments, two units of such dimer may be associated to form a tetramer (α2β2+α2β2).

A full-length FRIL can also include those comprising an amino acid sequence which (i) are substantially identical to the amino acid sequences set forth in SEQ ID NO: 1 (for example, at least 85% (e.g., at least 90%, 95% or 97%) identical to SEQ ID NO: 1); and (ii) are encoded by a nucleic acid sequence capable of hybridizing under at least moderately stringent conditions to any nucleic acid sequence encoding the FRIL set forth herein or capable of hybridizing under at least moderately stringent conditions to any nucleic acid sequence encoding the FRIL set forth herein, but for the use of synonymous codons (e.g. a codon which does not have the identical nucleotide sequence, but which encodes the identical amino acid).

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual (e.g., an individual at risk for the disease) prior to the onset of symptoms (e.g., in light of a history of symptoms and/or in light of genetic or other susceptibility factors). Treatment may also be continued after symptoms have resolved, for example, to delay or prevent recurrence. Specifically, the term "treating" or "treatment" refers to administering one or more anti-influenza A, B or C virus agent (e.g., the polypeptides described herein) to a subject (e.g., a human patient), who has influenza virus infection, a symptom of or a predisposition toward it, with the purpose to confer a therapeutic effect, e.g., to cure, relieve, alter, affect, ameliorate, or prevent the infection, the symptom of or the predisposition toward it. Such a subject can be identified by a health care professional based on results from any suitable diagnostic method.

An "effective amount" of a compound or any active ingredient as described herein of refers to an amount sufficient to elicit a desired biological response, i.e., treating the condition. As will be appreciated by those of ordinary skill in this art, the effective amount of a compound may vary depending on such factors as the desired biological endpoint, the pharmacokinetics of the compound, the condition being treated, the mode of administration, and the age and health of the subject. An effective amount encompasses therapeutic and prophylactic treatment.

Specifically, an "effective amount" is the amount of the anti-flu agent, either alone, or together with further doses, that produces one or more desired responses, e.g. inhibit viral replication. In the case of treating an infection caused by an influenza virus, the desired responses include inhibiting the progression of the disease or alleviating one or more symptoms associated with influenza infection. This may involve only slowing the progression of the disease temporarily, although more preferably, it involves halting the progression of the disease permanently. This can be monitored by routine methods. The desired responses to treatment of the disease or condition also can be delaying the onset or even preventing the onset of the disease or condition.

Effective amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The anti-flu agents (e.g. polypeptides) described herein may be formulated for administration by a route selected from the group consisting of oral, intravenous, intramuscular, intra-arterial, subcutaneous, intraventricular, transdermal, interdermal, rectal, intravaginal, intraperitoneal, topical, mucosal, nasal, buccal, enteral, sublingual, intratracheal and bronchial. In certain embodiments, the administration is by intratracheal and bronchial instillation. In certain embodiments, the administration may be by oral or nasal inhalation. In certain embodiments, the polypeptide described herein is formulated as an oral spray, a nasal spray, or an aerosol.

The anti-flu agents (e.g. polypeptides) described herein may be formulated as a quasi-drug for preventing an influenza viral infection. The quasi-drug may be a mist, a filter coating agent, a hand-wash, a mouthwash, a disinfectant, a shower foam, a water tissue, a detergent soap, an antiviral filter or an antiviral mask. In certain embodiments, the polypeptide is formulated as an antiviral mask that prevents the infectious viruses from entering the mask wearer's system from the mouth and/or the nose. In certain embodiments, the polypeptide is formulated as an antiviral filter that is capable of trapping the infectious viruses floating in the ambient air and inactivating the trapped viruses to clean the air.

The anti-flu agents (e.g. polypeptides) described herein can be mixed with a pharmaceutically acceptable carrier or excipient to form a pharmaceutical composition for use in inhibiting influenza viral replication and/or treating infection caused by an influenza virus. As used herein, "inhibiting," "inhibition," "inhibit," "inhibitor," and the like, refer to the ability of an anti-flu agent to reduce, slow, halt, or prevent activity of a particular biological process (e.g., influenza virus replication) in a cell relative to a control vehicle. In some instances, an anti-flu agent can inhibit the level of viral replication by at least 20% (e.g., 30%, 40%, 50%, 60%, 70%, 80%, 90%, or 95%).

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the anti-viral agents described herein, or more solubilizing agents, can be utilized as pharmaceutical carriers for delivery of the antiviral agents. Examples of other carriers include colloidal silicon dioxide, magnesium stearate, sodium lauryl sulfate, and D&C Yellow #10. See, e.g., Remington: The Science and Practice of Pharmacy, 21st Edition (Lippincott Williams & Wilkins, 2005); and Goodman and Gilman's "The Pharmacological Basis of Therapeutics", Tenth Edition, Gilman, J. Hardman and L. Limbird, eds., McGraw-Hill Press, 155-173, 2001.

Pharmaceutically acceptable excipients/carriers include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

In some examples, the subject in need of the treatment described herein can be a human patient has or is suspected of having infection with influenza virus, e.g., a wild-type influenza A virus (e.g., H1N1, H5N1, or H3N2) or with a mutant influenza virus, such as one that has a mutated NP protein, e.g., Y289H, Y52H, or Y52H/Y289H. A subject suspected of having infection caused by an influenza virus might show one or more symptoms of the infection, e.g., fever, cough, nasal congestion, body aches, fatigue, headache, watering eyes, diarrhea and/or abdominal pain.

Any of the pharmaceutical compositions described herein can be administered to a subject in need of the treatment via any conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrastemal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the anti-flu agent described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

A composition for oral administration can be any orally acceptable solid dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat.

Nos. 5,480,381; 5,599,302; 5,334,144; 5,993,412; 5,649, 912; 5,569,189; 5,704,911; 5,383,851; 5,893,397; 5,466, 220; 5,339,163; 5,312,335; 5,503,627; 5,064,413; 5,520, 639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

A nasal aerosol or inhalation composition can be prepared according to techniques well known in the art of pharmaceutical formulation. Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

In certain embodiments, an effective amount of an anti-flu agent as described herein for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In other embodiments, the anti-flu agent may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a polypeptide or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The polypeptide or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Also encompassed by the present disclosure are kits (e.g., pharmaceutical packs). The kits provided may comprise an inventive pharmaceutical composition or polypeptide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or polypeptide. In some embodiments, the inventive pharmaceutical composition or compound provided in the container and the second container are combined to form one unit dosage form.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety for the purposes or subject matter referenced herein.

EXAMPLES

In order that the invention described herein may be more fully understood, the following examples are set forth. It should be understood that these examples are for illustrative purposes only and are not to be construed as limiting this invention in any manner.

Example 1: Microneutralization Assay of *Lablab purpureus* Aqueous Extract

Figure 1:
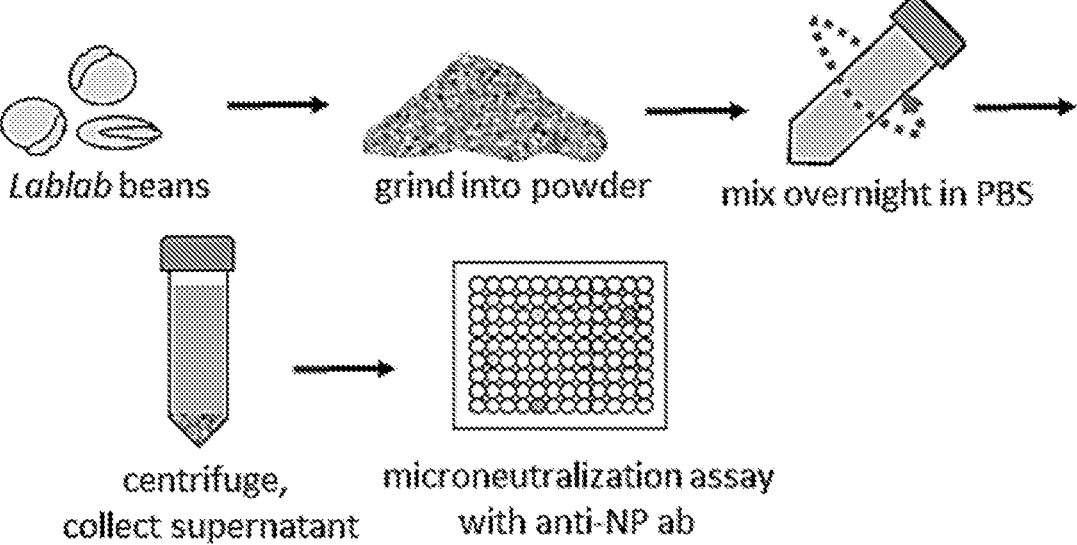
FIG. 1 shows anti-influenza activity of *Lablab purpureus* aqueous extract. *Lablab* beans were processed according to steps illustrated, and centrifuged supernatant microneutralization assay was done against either 10 or 100 $TCID_{50}$ of an A/California/7/09-like virus (H1N1 X181), A/Vietnam/1194/2004-like virus (H5N1 RG14), ANictoria/3/75-like virus (H3N2 vict), and A/Shanghai/1/2013-like virus (H7N9 shang).
Figure 1:
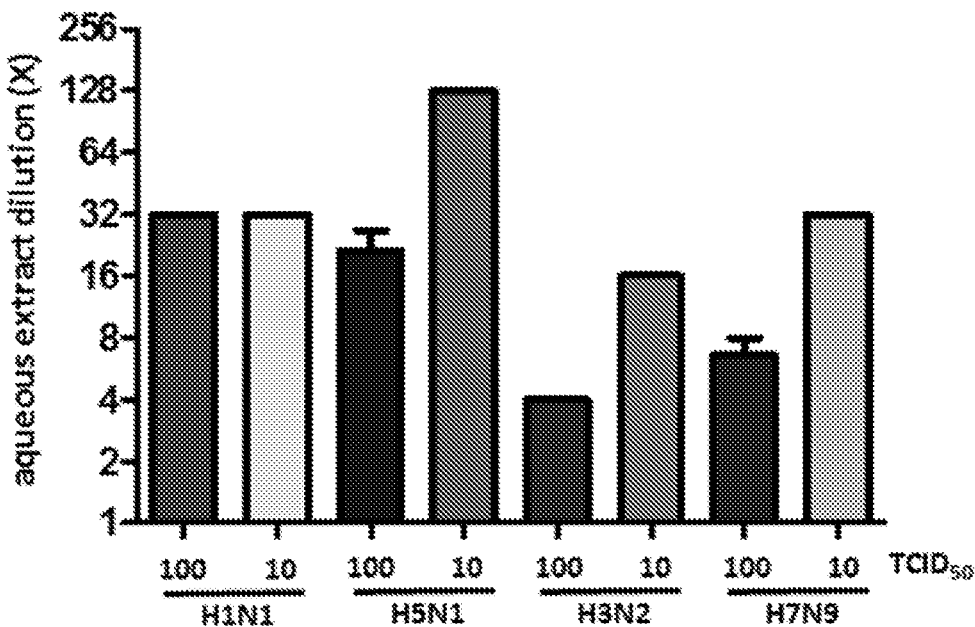

*Lablab* beans were collected, ground into powder, mixed with phosphate buffered saline (PBS) overnight and centrifuged to obtain the supernatant. See FIG. 1. Confirmation of the microneutralization (MN) ability of *Lablab purpureus* (also known as *Dolichos lablab*) aqueous extract against vaccine strains of A/California/7/2009-like (H1N1 X181), A/Vietnam/1194/2004-like (H5N1 RG14), A/Victoria/361/2011-like (H3N2), and A/Shanghai/2/2013-like (H7N9 RG32A) viruses was carried out using established methods (FIG. 1). All vaccine strains were from Adimmune Corporation, and cell infection detected by polyclonal anti-NP antibodies. Results show the aqueous extract of *Lablab purpureus* had a broad spectrum of neutralization ability, with MN titers across both group 1 and group 2 viruses (FIG. 1B).

Figure 2:
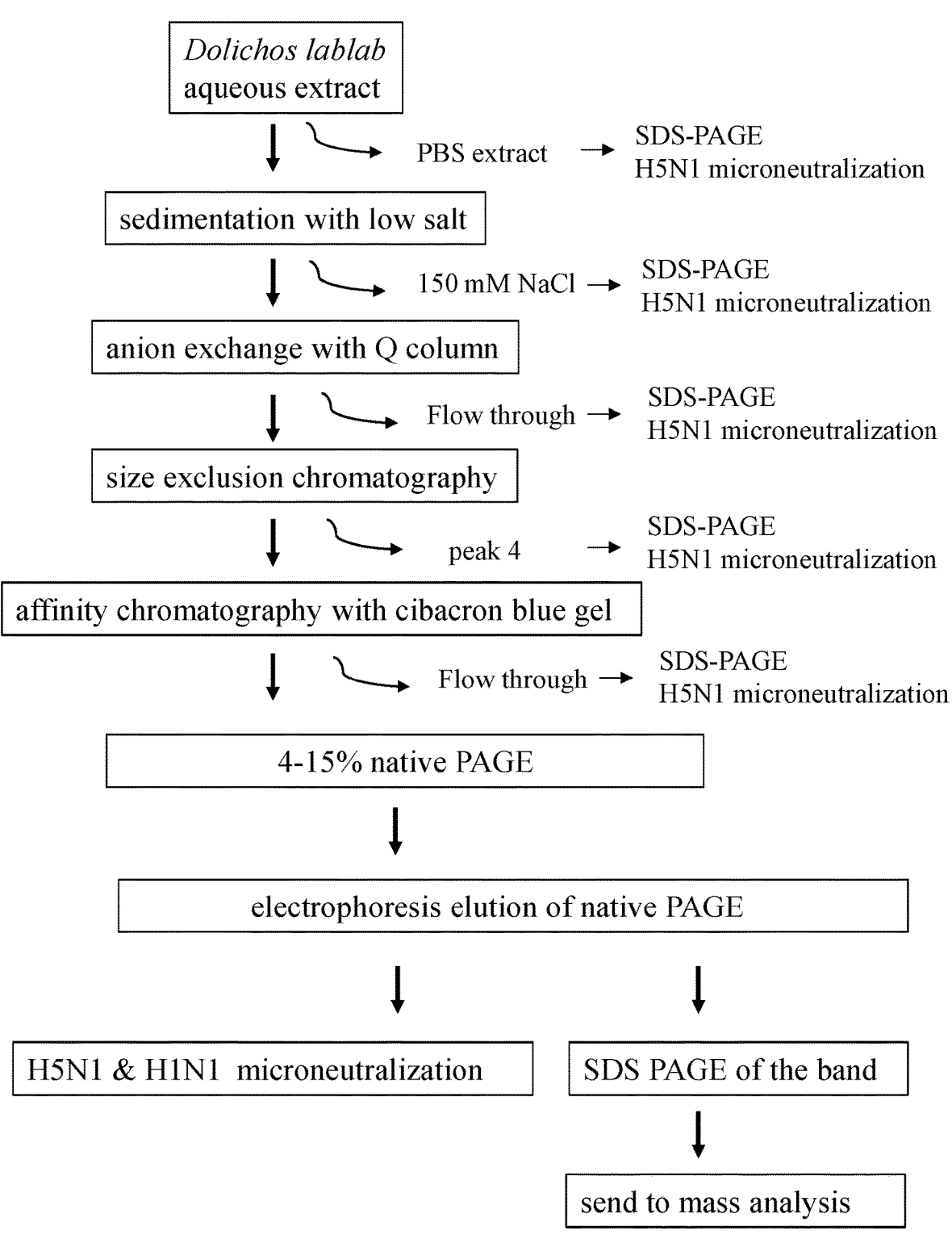
FIG. 2 shows flowchart of *Lablab purpureus* aqueous extract exploratory purification process. Flowchart of extraction, sedimentation, anion exchange, size exclusion and affinity chromatography steps, with collected fractions. Confirmation of the six PAGE bands responsible for neutralization by native gel electrophoresis, followed by gel elution and microneutralization assay of the eluted bands. Arrows represent progression.

Example 2: Viral Neutralization Agent Isolated from *Lablab purpureus* Aqueous Extract Since neutralization titers occurred in the aqueous extract, a number of protein purification steps were utilized to isolate the viral neutralization agent. Sedimentation and resuspension processes with low salt buffer were first applied, then followed by an anion exchange, gel filtration and affinity chromatography with Affigel blue media. MN with an A/Vietnam/1194/2004-like virus (H5N1 RG14) was carried out in every step to verify the collected fractions, and sodium dodecylsulfate polyacrylamide gel electrophoresis (SDS PAGE) was carried out to visualize protein compositions (FIG. 2).

Six major bands and four minor bands were present after the above-mentioned purification steps. Five out of the six major bands are in the range of MW at 12~20 kDa with one band with MW at 34 kDa. The protein mixture was analyzed in a native PAGE. Major band was collected and eluted by electrophoresis under denaturing conditions with sodium dodecylsulfate (SDS). Six bands were observed in the SDS PAGE. To further confirm the purification steps, the native PAGE-eluted protein was tested for anti-influenza activity by MN with H1N1 and H5N1 virus strains, and results show the protein retains its neutralization activity (FIG. 2).

Figure 4A:
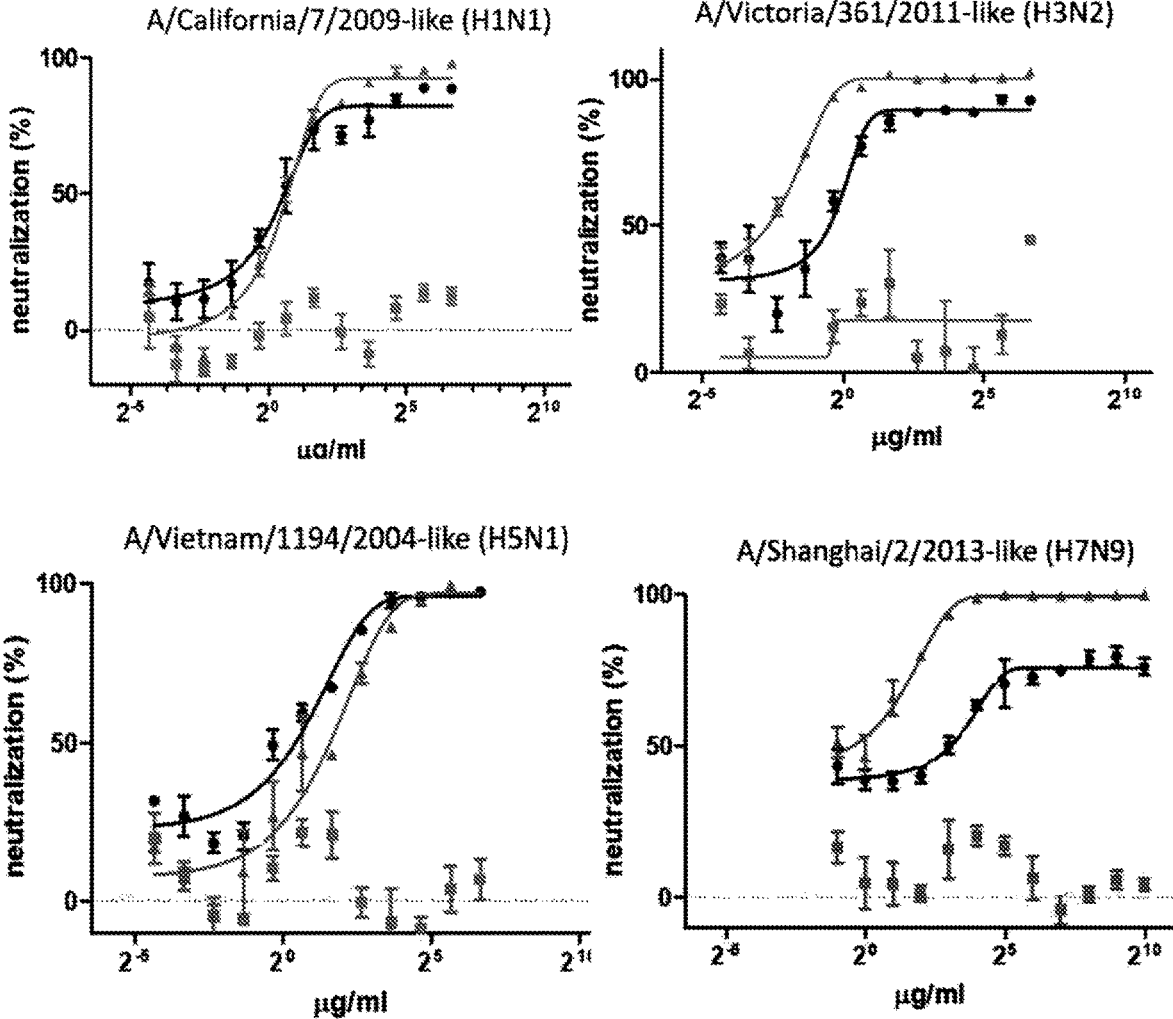
FIG. 4A shows the results of microneutralization assays of FRIL (-●-), ConA (-▲-) and pvFRIL against A/California/7/2009-like (H1N1), A/Victoria/361/2011-like (H3N2), A/Vietnam/1194/2004-like (H5N1), and A/Shanghai/2/2013-like (H7N9) viruses.
Figure 4B:
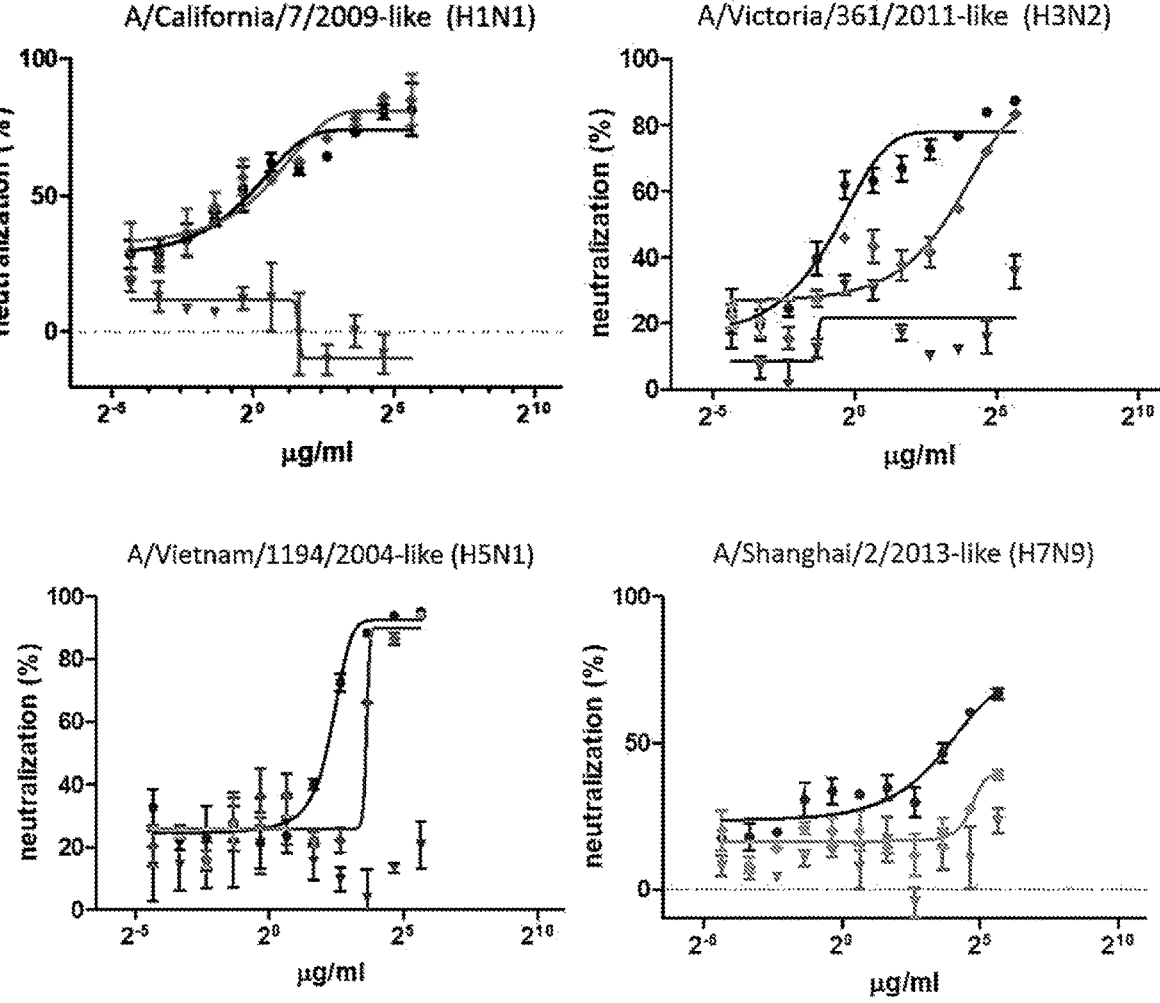
FIG. 4B shows the results of microneutralization assays of FRIL (-●-), bnab FI6v3 (-◆-), and OTC (-▼-) against A/California/7/2009-like (H1N1), A/Victoria/361/2011-like (H3N2), A/Vietnam/1194/2004-like (H5N1), and A/Shanghai/2/2013-like (H7N9) viruses.

To analyze the purified proteins, in-gel digestion was applied to collect all six bands for mass spectrometry analysis. The results confirmed the purified protein is Flt3 Receptor Interacting Lectin (FRIL).

hai/2/2013-like (H7N9) viruses. FIG. 4B show the results of microneutralization assays of FRIL (-●-), bnab FI6v3 (-♦-) and OTC (-▲-) against A/California/7/2009-like (H1N1), A/Victoria/361/2011-like (H3N2), A/Vietnam/1194/2004-like (H5N1), and A/Shanghai/2/2013-like (H7N9) viruses.

FRIL and ConA were able to achieve comparable levels of $IC_{50}$. Microneutralization activities of bnab FI6v3 against group 1 viruses (H1N1 and H5N1) and H3N2 were indicated by $IC_{50}$ in the range of 10~100 nm, while bnab FI6v3 exhibited considerably higher $IC_{50}$ against H7N9. It was found that pvFRIL was not able to neutralize any of influenza virus strains tested. OTC appeared to have no neutralization ability against influenza virus strains tested, perhaps because its mechanism of action renders it unsuitable for standard microneutralization tests [59]. Able 2 is a comparison of microneutralization activities for viral neutralization agents against various influenza virus strains. Table 1 and Table 2 list the summary of microneutralization activities for various viral neutralization agents against multiple influenza virus strains.

TABLE 1

| Influenza neutralization activity of FRIL and FI6v3 | | | |
|---|---|---|---|
| Influenza strains | # of N-glycosylation sites on hemagglutinin[a] | FRIL $EC_{50}$[b] μg/mL (nM) | FI6v3 $EC_{50}$[b] μg/mL (nM) |
| A/California/07/2009-like (H1N1) | 4 | 0.74 (6.60) | 0.77 (5.13) |
| A/New Caledonia/20/1999 (H1N1) | 7 | 0.52 (4.64) | 15.44 (103.93) |
| A/WSN/1933 (H1N1) | 2 | 3.06 (27.30) | <0.03 (<0.20) |
| A/Puerto Rico/8/1934 (H1N1) | 4 | >29.34 (>261.73) | 0.77 (5.13) |
| A/Victoria/361/2011-like (H3N2) | 6 | 0.55 (4.91) | 6.40 (42.67) |
| A/Wisconsin/67/2005-like (H3N2) | 5 | 4.29 (38.27) | >35.71 (>238.07) |
| A/Vietnam/1194/2004-like (H5N1) | 3 | 2.74 (24.44) | 8.78 (58.53) |
| A/Shanghai/02/2013-like (H7N9) | 3 | 9.85 (87.87) | >35.71 (>238.07) |
| B/Brisbane/60/2008-like | 4 | 1.80 (16.06) | >35.71 (>238.07) |
| B/Florida/4/2006-like | 4 | 25.94 (231.40) | >35.71 (>238.07) |
| B/Malaysia/2506/2004-like | 4 | 0.94 (8.39) | >35.71 (>238.07) |

[a]number of N-glycosylation sites on viral hemagglutinin (HA) predicted with NetNGlyc 1.0, potential >0.5 and jury agreement or potential >0.75 (++)
[b]effective concentration required to inhibit influenza NP protein production by 50% in MDCK cells (absolute $EC_{50}$)

Figure 3:
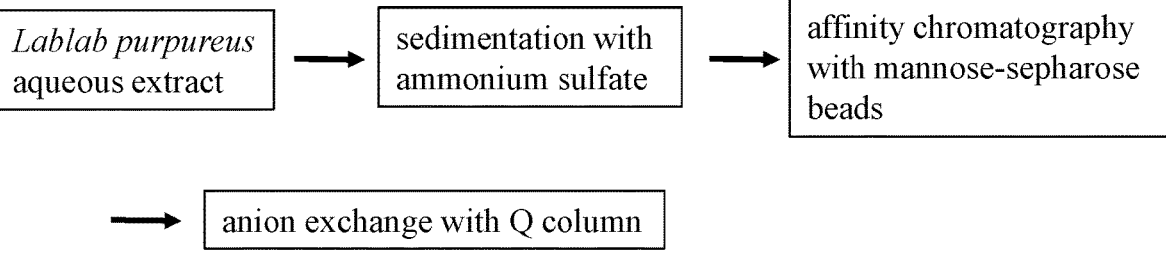
FIG. 3 shows the purification procedure of FRIL and hemagglutination activity of FRIL. Flowchart of extraction, sedimentation, affinity chromatography and anion exchange steps. Fractionation of purified FRIL on a 14% SDS PAGE, stained with Rapid stain. Hemagglutination activity of FRIL on turkey red blood cells during various steps of the purification process.
Figure 3:
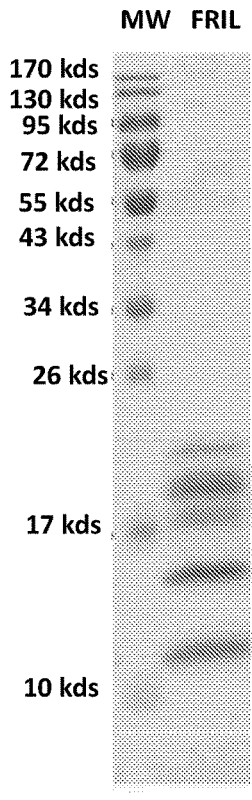

To further purify the FRIL, sedimentation and resuspension processes were performed using 60% ammonium sulfate, followed by an affinity chromatography with mannose-sepharose beads. Next, an anion exchange with Q column starting at 150 mM NaCl was applied to deplete the non-specific bands having the MW at 55~72 kD. The purified FRIL was collected in the flow through during the anion exchange chromatography. The yield of purified FRIL was greater than 4 mg/g bean powder, and the purity of FRIL was greater than 95% determined by hemagglutination assay (FIG. 3).

Example 3: Microneutralization Activities of Viral Neutralization Agents

Microneutralization assays were performed for FRIL, pvFRIL (*Phaseolus vulgaris* Flt3 receptor-interacting lectin), ConA (a prototypical legume lectin), FI6v3 (a broadly-neutralizing influenza antibody, bnab), and oseltamivir carboxylate (OTC), an active metabolite of the commercially available neuraminidase inhibitor oseltamivir phosphate. FIG. 4A shows the results of microneutralization assays of FRIL (-●-), ConA (-]-), and pvFRIL (-■-) against A/California/7/2009-like (H1N1), A/Victoria/361/2011-like (H3N2), A/Vietnam/1194/2004-like (H5N1), and A/Shang-

Example 4: Glycan Binding Characteristic of Viral Neutralization Agents

Figure 5:
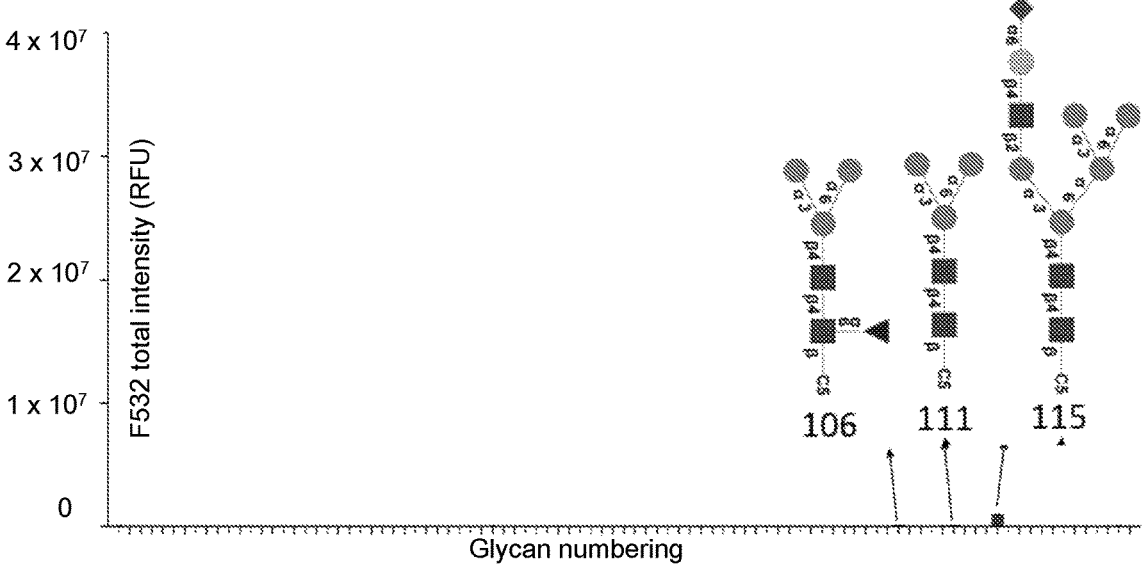
FIG. 5 shows FRIL glycan array performed with Cy3 labeling (1:1 molar ratio). A total of 191 sugars were incubated against 12.5 μg/ml FRIL-Cy3 and results scanned with wavelength 532 nm.
Figure 5:
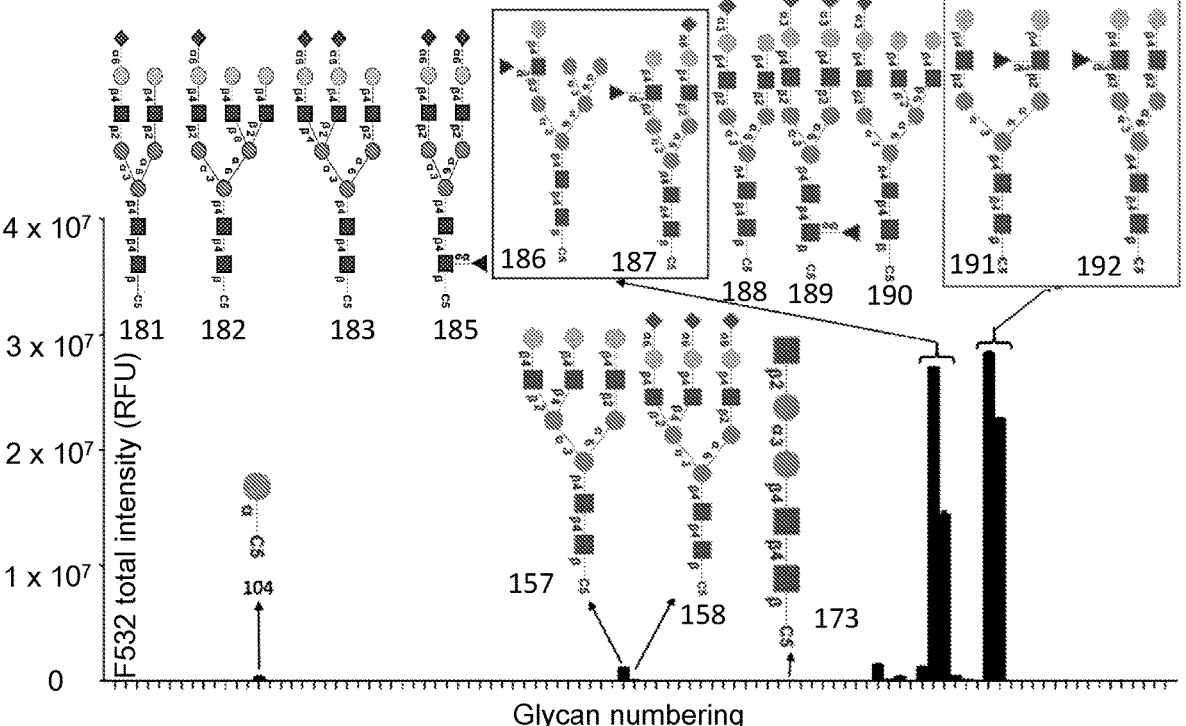

Previous literature reports merely used Hemagglutination Inhibition Test (HAI) to determine FRIL monosaccharide affinity [13]. A comprehensive glycan analysis was conducted using glycan array with Cy3-labeled FRIL (FIG. 5). Surprisingly, FRIL showed rather weak binding to single α-linked mannose residues and glcNac-linked trimannose core. Instead, FRIL showed strong binding affinity to either a 1-3 or α 1-6 linked Manβ1-2GlcNacβ1-4(Fucα1-3)Gal tetrasaccharide moiety. There was no detectable binding to high mannose oligosaccharides Man5 and Man9. To confirm the finding, differentially-glycosylated egg-based influenza viruses (A/California/7/2009-like virus, H1N1 X181) were generated by treating the influenza viruses with a mannosidase I inhibitor kifunensine (KIF) during the viral infection, followed by the treatment with a high mannose-cleaving glycosidase Endo H. Four types of viral particles were generated for comparison, including (1) non-treated (complex, CX, and high mannose-type, HM, glycans), (2) KIF-treated (HM only), (3) Endo H-treated (CX and monoglycosylated, MG, glycans), and (4) KIF/Endo H-treated (MG only). These viruses were then purified by sucrose density gradient centrifugation (SDG), and tested by microneutralization assays according to the methods described herein. In accordance with glycan array results, FRIL exhibited the most potent neutralization ability against non-treated CX type virus particles, whereas FRIL showed no neutralization ability against HM and MG viruses at the concentration up to 100 μg/ml. This is in stark contrast to the well-known ConA which showed the greatest neutralization effect on HM viruses. Bnab FI6v3 showed comparable neutralization on FG, CX and HM viruses and vastly improved neutralization on MG (FIG. 6).

Example 5: Anti-Influenza Activity of FRIL Related to Lectin Function

To determine whether FRIL's anti-influenza activity is related to its lectin function. The following was carried out: saturation of FRIL with a known ligand α-mannopyranoside (FIG. 7), and inhibition of FRIL binding site by lysine residue conjugation with the cyanine dye Cy3 (FIG. 7), which has previously been reported to decrease FRIL hemagglutination ability by 95% [47]. Results showed both methods nearly completely inhibited FRIL's hemagglutination and MN ability (FIG. 7), suggesting that FRIL's anti-influenza activity is indeed related to its lectin function.

Example 6: Mechanism of Action

To explore the mechanism of action of FRIL, a Hemagglutination Inhibition Test (HAI) was carried out. Since FRIL has a relatively weak hemagglutination activity (1.25~0.8 HAU/μg, FIG. 9) compared to the hemagglutination activity of an influenza hemagglutinin (80~1000 HAU/ μg for recombinant HA trimers, data not shown), an HAI assay was performed using sub-agglutinating (>0.5 μg) concentrations of FRIL, which is well above its neutralization titer (0.20~0.018 μg/well). Results showed FRIL exhibited no HAI activity against 4 HAUs of H1N1, H3N2, H5N1 or H7N9 viruses (data not shown). This result suggests FRIL does not act by inhibiting virus HA binding to cellular receptors.

A trypsin susceptibility assay (TSA) [48] was used to test for inhibition of virus envelope fusion with endosome. The fusion event mediated by influenza hemagglutinin requires a pH-dependent conformational change. The influenza hemagglutinin, while normally quite resistant to trypsin digestion, becomes more susceptible after undergoing this conformation change, and TSA utilizes this property to visualize intact or digested HA on an SDS PAGE. Many anti-influenza bnabs inhibit this conformational change under low-pH conditions by steric hinderance, such as FI6. The results showed the bnab FI6 was able to inhibit influenza HA conformational change at pH 5.0 under 1:1, 1:2 and 1:4 molar ratios, while FRIL did not have this effect even at a 1:10 molar ratio (FIG. 8). This indicates FRIL does not act by inhibiting virus entry through HA-mediated fusion with endosome.

To examine whether FRIL works by cross-linkage of viral glycoproteins or agglutination of virus particles, the first thing we have to determine is carbohydrate binding domain (CBD) polyvalency. According to previous studies [17], FRIL and very likely pvFRIL only have one CBD per monomer, yet a lectin needs at least two CBDs to cross-link or agglutinate glycoproteins. Therefore, a dimer or tetramer quaternary structure is essential for this virus-neutralizing hypothesis to work. However, preliminary data shows when FRIL is loaded onto a Superdex s200 column, the protein comes out at approximately 30 kDa according to protein standards, a molecular weight that indicates monomers. Later, gel filtration done on ConA and pvFRIL show that they both interact with the dextran beads in the column, pvFRIL coming out impossibly late and ConA needing a mannose elution step to come out. This indicated that FRIL may have such interaction.

To get a more accurate determination of FRIL stoichiometry, multi-angle light scattering (MALS, without size exclusion due to the aforementioned dextran interactions) and dynamic light scattering (DLS) were applied. DLS data show a sharp FRIL peak at approx. 5~7 nm in size, overlapping with the canonical tetramer of ConA (FIG. 9A). In MALS, although results are variable due to a lack of size-exclusion beforehand, also show FRIL at roughly 113.5 kDa, which approximates to a tetrameric state (FIG. 9B).

Example 7: Preparation of Mono-Glycosylated Influenza Viruses for Influenza Virus Aggregation Assay SDG-purified A/California/7/2009-like virus (H1N1 X181) was first treated with kifunensine and Endo H to generate mono-glycosylated influenza virus particles. A large amount of FRIL was added, hoping to induce influenza virus aggregation. Surprisingly, FRIL-induced aggregation was not formed with mono-glycosylated virus particles was formed with high mannose type and complex/high mannose type virus particles, but was not formed with mono-glycosylated virus particles (FIG. 10A). Another observation of aggregation happened when FRIL was added in a 1:3 molar ratio to H1N1 recombinant hemagglutinin. Visible precipitant formed in the tube, and both FRIL and HA bands were observed when these sediments were washed and visualized on an SDS PAGE (FIG. 10B). Also see Table 2.

TABLE 2

| Influenza particle aggregation by EM | | |
|---|---|---|
| FRIL concentration | n^a | aggregation (%)^b |
| 0 μg/ml | 493 | 13.39% |
| 2 μg/ml | 573 | 22.69% |
| 8 μg/ml | 482 | 54.77% |
| 32 μg/ml | 522 | 65.52% |

^a number of virions on 20 images per concentration, taken from four corners of 5 grids. Particle counts at FRIL concentrations above 32 μg/ml proved difficult due to formation of large aggregates.
^b virions that directly contact each other were considered aggregated.

Example 8: Neutralization Effect of FRIL on Viruses

To determine whether FRIL targets the virus or the cell, we pretreated MDCK cells with one agent (either FRIL or virus) for 1 hour. The cells were then washed to remove any unbound FRIL or virus, and incubated with the other agent (if FRIL was used during the pretreatment step then the incubation step is with the virus, and vice versa) for the next 18~20 hrs. In this way FRIL does not come into contact with the virus, only the cell. Results show FRIL must be co-incubated with the virus to have neutralization effect, which suggests FRIL works on the virus and not on the cell (FIG. 11). This effect was also observed in ConA (FIG. 11).

Example 9: Administration of FRIL Protects Mice from a Lethal Dose of H1N1 X-181 Influenza Virus Challenge BALB/c mice were given 5 or 50 μg of FRIL 4 hours before lethal dose (5 LD50) influenza virus intranasal infection of H1N1 X-181, afterwards 2 different doses of FRIL were given intranasally daily for 8 days. Each group has 10 mice. The survival and body weight change were observed for 21 days. Control group which received PBS died on day 5-8. FRIL 0.01 mg group has survival of 10%, 0.1 mg group 70%. See FIG. 12. The mouse model indicate that the lectin can significantly increase the survival of mice in a dose dependent manner.

Hemagglutination Assay

Influenza virus particles have an envelope protein, hemagglutinin (HA), which binds to sialic acid receptors on cells. The virus particles also bind to erythrocytes (red blood cells), causing the formation of a lattice. This property is called hemagglutination, and is the basis of a rapid assay to determine levels of influenza virus present in a sample. To conduct the assay, two-fold serial dilutions of a virus are prepared, mixed with a specific amount of red blood cells, and added to the wells of a plastic tray. The red blood cells that are not bound by influenza virus sink to the bottom of a well and form a button. The red blood cells that are attached to virus particles form a lattice that coats the well. The assay can be performed within 30 minutes, and is therefore a quick indicator of the relative quantities of virus particles.

Hemagglutination Inhibition Assay

The basis of the Hemagglutination Inhibition (HI) assay is that binding agents (e.g. antibodies) to influenza virus will prevent attachment of the virus to red blood cells. Therefore hemagglutination is inhibited when antibodies are present. The highest dilution of serum that prevents hemagglutination is called the HI titer of the serum. If the serum contains no antibodies that react with the new H1N1 strain, then hemagglutination will be observed in all wells. Likewise, if antibodies to the virus are present, hemagglutination will not be observed until the antibodies are sufficiently diluted.

Microneutralization Assay

Microneutralization assay is a highly sensitive and specific assay to detect the presence of influenza virus infection in MDCK cells, which can be performed on a microplate in combination with anti-influenza NP ELISA. The lack of infection indicates the virus applied to MDCK cells have been neutralized by a specific concentration of our test agent, and by using sequential dilutions of our test agent the effective concentration that achieves 50% neutralization (EC50) of the influenza virus strain can be calculated. The micorneutralization assay is both less laborious and prone to human error compared to conventional neutralization assays that rely on observation of cytopathic effects.

---

Sequence Information

```
Flt3 receptor interacting lectin (FRIL) protein
from Lablab purpureous (SEQ ID NO: 1)
MFPSKVKSAQ SLSFSFTKFD PNQEDLIFQG HATSTNNVLQ
VTKLDSAGNP VSSSAGRVLY SAPLRLWEDS AVLTSFDTII
NFEISTPYTS RIADGLAFFI APPDSVISYH GGFLGLFPNA
NTLNNSSTSE NQTTTKAASS NVVAVEFDTY LNPDYGDPNY
IHIGIDVNSI RSKVTAKWDW QNGKIATAHI SYNSVSKRLS
VTSYYAGSKP ATLSYDIELH TVLPEWVRVG LSASTGQDKE
RNTVHSWSFT SSLWTNVAKK ENENKYITRG VL N-terminal domain (beta subunit) (SEQ ID NO: 2)
AQSLSFSFTK FDPNQEDLIF QGHATSTNNV LQVTKLDSAG
NPVSSSAGRV LYSAPLRLWE DSAVLTSFDT IINFEISTPY
TSRIADGLAF FIAPPDSVIS YHGGFLGLFP NAN
```

-continued

Sequence Information

```
loop domain (SEQ ID NO: 3)
TLNNSSTSEN QTTTKAA

C-terminal domain (alpha subunit) (SEQ ID NO: 4)
SSNVVAVEFD TYLNPDYGDP NYIHIGIDVN SIRSKVTAKW
DWQNGKIAT AHISYNSVSK RLSVTSYYAG SKPATLSYDI
ELHTVLPEWV RVGLSASTG QDKERNTVHS WSFTSSLWTN
VAKKENENKY ITRGVL Signal peptide (SEQ ID NO: 5)
MFPSKVKS
```

---

REFERENCES

1. Wu C Y, Lin C W, Tsai T I, Lee D C, Chuang H Y, Chen J B, Tsai M H, Chen B R, Lo P W, Liu C P, Shivatare V S, Wong C H. Influenza A Surface Glycosylation and Vaccine Design. *Proc Natl Acad Sci* 2017, 144(2), p 280-285.

2. Job E R, Deng Y M, Barfod K K, Tate M D, Caldwell N, Reddiex S, Maurer-Stroh S, Brooks A G, Reading P C. Addition of Glycosylation to Influenza A Virus Hemagglutinin Modulates Antibody-Mediated Recognition of H1N1 2009 Pandemic Viruses. *J Immunol* 2013, 190, p 2169-2177.

3. Tate M D, Job E R, Deng Y M, Gunalan V, Maurer-Stroh S, Reading P C. Playing Hide and Seek: How Glycosylation of the Influenza Virus Hemagglutinin Can Modulate the Immune Response to Infection. Viruses 2014, 6, p 1284-1316.

4. Balzarini J. Carbohydrate-Binding Agents: A Potential Future Cornerstone for the Chemotherapy of Enveloped Viruses? Antivir Chem Chemother 2007, 18, p 1-11.

5. Mitchell C A, Ramessar K, O'Keefe B R. Antiviral Lectins: Selective Inhibitors of Viral Entry. Antivir Res 2017, 142, p 37-54.

6. O'Keefe B R, Smee D F, Turpin J A, Saucedo C J, Gustafson K R, Mori T, Blakeslee D, Buckheit R, Boyd M R. Potent Anti-Influenza Activity of Cyanovirin-N and Interactions with Viral Hemagglutinin. Antimicrob Agents Chemother 2003, 47, p 2518-2525.

7. Smee D F, Baily K W, Wong M H, O'Keefe B R, Gustafson K R, Mishin V P, Gubareva L V. Treatment of Influenza A (H1N1) Virus Infections in Mice and Ferrets with Cyanovirin-N. Antivir Res 2008, 80, p 266-271.

8. Swanson M D, Boudreaux D M, Salmon L, Chigh J, Winter H C, Meagher J L, Andre S, Murphy P V, Oscarson S, Roy R, King S, Kaplan M H, Goldstein I J, Tarbet E B, Hurst B L, Smee D F, de la Fuente C, Hoffmann H H, Xue Y, Rice C M, Schols D, Garcia J V, Stuckey J A, Gabius H J, Al-Hashimi H M, Markovitz D M. Engineering a Therapeutic Lectin by Uncoupling Mitogenicity from Antiviral Activity. *Cell* 2015, 163, p 746-758.

9. Loris R, Hamelryck T, Bouckaert J, Wyns L. Legume Lectin Structure. *Biochimica et Biophysica Acta* 1998, 1383, p 9-36.

10. Delbaere L T, Vandonselaar M, Prasad L, Quail J W, Wilson K S, Dauter Z. Structures of the Lectin I V of *Griffonia simplicifolia* and Its Complex with the Lewis B Human Blood Group Determinant at 2.0 A Resolution. *J Mol Biol* 1993, 230, p 950-965.

11. Gowda L R, Savithri H S, Rao D R. The Complete Primary structure of a Unique Mannose/Glucose-Specific Lectin from Field Bean (*Dolichos lablab*). *J Biol Chem* 1994, 269, p 18789-18793.

12. Rajasekhar B T, Kumar N S. A New Unusual Galactose Specific Lectin from the Seeds of Indian *Lablab* Beans. *Curr Sci* 1998, 75, p 840-842.

13. Mo H, Younus M, Moore J G, Goldstein I J. Purification and Characterization of *Dolichos lablab* Lectin. Glyco-biology 1999, 9, p 173-179.

14. Latha V L, Rao R N, Nadimpalli S K. Affinity Purification, Physicochemical and Immunological Characterization of a Galactose-Specific Lectin from the Seeds of *Dolichos lablab* (Indian *Lablab* beans). *Protein Expr Purif* 2006, 45, p 296-306.

15. Kanade S R, Rao D H, Hegde R N, Gowda L R. The Unique Enzymatic Function of Field Bean (*Dolichos lablab*) D-Galactose Specific Lectin: a Polyphenol Oxidase. *Glycoconj J* 2009, 26, p 535-545.

16. Colucci G, Moore J G, Feldman M, Chrispeels M J. cDNA Cloning of FRIL, a Lectin from *Dolichos lablab*, That Preserves Hematopoietic Progenitors in Suspension Culture. *Proc Natl Acad Sci* 1999, 96, p 646-650.

17. Hamelryck T W, Moore J G, Chrispeels M J, Loris R, Wyns L. The Role of Weak Protein-Protein Interactions in Multivalent Lectin-Carbohydrate Binding: Crystal Structure of Cross-Linked FRIL. *J Mol Biol* 2000, 299, p 875-883.

18. Kumar G, Polentz G, Schulte M, Mormann M, Nadimpalli S K. N-Glycan Analysis of Mannose/Glucose Specific Lectin from *Dolichos lablab* Seeds. *Int J Biol Macromol* 2014, 69, p 400-407.

19. Favero J, Miguel F, Dornand J, Mani J C. Determination of Mitogenic Properties and Lymphocyte Target Sites of *Dolichos lablab* Lectin (DLA): Comparative Study with Concanavalin A and Galactose Oxidase Cell Surface Receptors. *Cell Immunol* 1988, 112, p 302-314.

20. Vigneshwaran V, Thirusangu P, Vijay Avin B R, Krishna V, Pramod S N, Prabhakar B T. Immunomodulatory Glc/Man-Directed *Dolichos lablab* Lectin (DLL) Evokes Anti-tumour Response in vivo by Counteracting Angiogenic Gene Expressions. *Clin Experi Immunol* 2017, 189, p 21-35.

21. Yao H, Xie X, Li Y, Wang D, Han S, Shi S, Nan X, Bai C, Wang Y, Pei X. Legume Lectin FRIL Preserves Neural Progenitor Cells in Suspension Culture in Vitro. *Clin Dev Immunol* 2008, 2008, 531317.

22. Sato Y, Morimoto K, Kubo T, Sakaguchi T, Nishizono A, Hirayama M, Hori K. Entry Inhibition of Influenza Viruses with High Mannose Binding Lectin ESA-2 from the Red Alga *Eucheuma serra* through the Recognition of Viral Hemagglutinin. *Mar Drugs* 2015, 13(6), p 3454-3465.

23. Moore J G, Fuchs C A, Hata Y S, Hicklin D J, Colucci G, Chrispeels M J, Feldman M. A New Lectin in Red Kidney Beans Called PvFRIL Stimulates Proliferation of NIH 3T3 Cells Expressing the Flt3 Receptor. *Biochimica et Biophysica Acta* 2000, 1475, p 216-224.

24. Allzadeh H, Leung D W M, Cole A L J. Conidiogenic Effects of Mannose-Binding Lectins Isolated from Cotyledons of Red Kidney Bean (*Phaseolus vulgaris*) on *Alternaria alternata*. Phytochemistry 2011, 72, p 94-99.

25. Nicolson G L. The Interactions of Lectins with Animal Cell Surfaces. *Int Rev Cytol* 1974, 39, p 89-190.

26. Borrebaeck C A K, Carlsson R. Lectins as Mitogens. Adv Lectin Res 1989, 2, p 1-27.

27. Knolle P A, Gerken G, Loser E, Dienes H P, Gantner F Tiegs G, Meyer zum Buschenfelde K, Lohse A W. Role of Sinusoidal Endothelial Cells of the Liver in Concanavalin A-Induced Hepatic Injury in Mice. *Hepatology* 1996, 24(4), p 824-829.

28. Clinicaltrials.gov [Internet]. Bethesda (Md.), National Library of Medicine (US). 2017 October 1—. Identifier NCT02875119, Study to Evaluate the Safety of Griffithsin in a Carrageenan Gel in Healthy Women; 2016 August 23 [cited 2018 May 30], [about 5 screens]. Available from: https://clinicaltrials.gov/ct2/show/ NCT02875119?term=Griffithsin&rank=1.

29. Hopper J T S, Ambrose S, Grant O C, Krumm S A, Allison T M, Degiacomi M T, Tully M D, Pritchard L K, Ozorowski G, Ward A B, Crispin M, Doores K J, Woods R J, Benesch J L P, Robinson C V, Struwe W B. The Tetrameric Plant Lectin BanLec Neutralizes HIV Through Bidentate Binding to Specific Viral Glycans. *Cell Structure* 2017, 25, p 773-782.

30. Maass B L, Knox M R, Venkatesha S C, Angessa T T, Ramme S, Pengelly B C. *Lablab purpureus*—A Crop Lost for Africa? *Trop Plant Biol* 2010, 3(3), p 123-135.

31. Su B, Wurtzer S, Rameix-Welti M A, Dwyer D, van der Werf S, Naffakh N, Clavel F, Labrosse B. Enhancement of the Influenza A Hemagglutinin (HA)-Mediated Cell-Cell Fusion and Virus Entry by the Viral Neuraminidase (NA). *PLoS One* 2009, 4(12), e8495.

32. Xiong X, Martin S R, Haire L F, Wharton S A, Daniels R S, Bennett M S, McCauley J W, Collins P J, Walker P A, Skehel J J, Gamblin S J. Receptor binding by an H7N9 influenza virus from humans. *Nature* 2013, 499, p 496-499.

33. Guran A, Ticha M, Filka K, Kocourek J. Isolation and Properties of a Lectin From the Seeds of the Indian Bean or *Lablab* (*Dolichos lablab* L.). *Biochem J* 1983, 209, p 653-657.

34. Mori T, O'Keefe B R, Sowder R C II, Bringans S, Gardella R, Berg S, Cochran P, Turpin J A, Buckheit R W Jr. Isolation and Characterization of Griffithsin, a Novel HIV-Inactivating Protein, From the Red Alga *Griffithsia* sp. *J Biol Chem* 2005, 280(10), p 9345-9353.

35. Becht H, Rott R. Purification of Influenza Virus Hemagglutinin by Affinity Chromatography. *Med Microbiol Immunol* 1972, 158, p 67-70.

36. Barrientos L G, Matei E, Lasala F, Delgado R, Gronenborn A M. Dissecting Carbohydrate-Cyanovirin-N Binding by Structure-Guided Mutagenesis: Functional Implications for Viral Entry Inhibition. *Protein Eng Des Sel* 2006, 19(12), p 525-535.

37. Bashirova A A, Geijtenbeek T B H, van Duijnhoven G C F, van Vliet S J, Eilering J B G, Martin M P, Wu L, Martin T D, Viebig N, Knolle P A, KewalRamani V N, van Kooyk Y, Carrington M. A Dendritic Cell-Specific Intercellular Adhesion Molecule 3-Grabbing Nonintegrin (Dc-Sign)-Related Protein Is Highly Expressed on Human Liver Sinusoidal Endothelial Cells and Promotes HIV-1 Infection. *J Exp Med* 2001, 193(6), p 671-678.

38. Hamelryck T W, Loris R, Bouckaert J, Dao-Thi M H, Strecker G, Imberty A, Fernandez E, Wyns L, Etzler M E. Carbohydrate Binding, Quaternary Structure, and a Novel Hydrophobic Binding Site in Two Legume Lectin Oligomers from *Dolichos biflorus*. *Mol Biol* 1999, 286, p 1161-1177.

39. Swanson M D, Winter H C, Goldstein I J, Markovitz D M. A Lectin Isolated from Bananas is a Potent Inhibitor of HIV Replication. *J Biol Chem* 2010, 285(12), p 8646-8655.

29

40. Bloom J D, Gong L I, Baltimore D. Permissive Secondary Mutations Enable the Evolution of Influenza Oseltamivir Resistance. *Science* 2010, 328(5983), p 1272-1275.

41. Nelson M I, Simonsen L, Viboud C, Miller M A, Holmes E C. The Origin and Global Emergence of Adamantane Resistant A/H3N2 Influenza Viruses. *Virology* 2009, 388 (2), p 270-278.

42. Dowdel W R. The Principles of Disease Elimination and Eradication. *Bull World Health Organ* 1998, 76 suppl 2, p 22-25.

43. Gordts S C, Renders M, Ferir G, Huskens D, Van Damme E J, Peumans W, Balzarini J, Schols D. NICTABA and UDA, Two GlcNAc-Binding Lectins with Unique Antiviral Activity Profiles. *J Antimicrob Chemother* 2015, 70(6), p 1674-1685.

44. Bolmstedt A J, O'Keefe B R, Shenoy S R, McMahon J B, Boyd M R. Cyanovirin-N Defines a New Class of Antiviral Agent Targeting N-Linked, High-Mannose Glycans in an Oligosaccharide-Specific Manner. *Mol Pharmacol* 2001, 59(5), p 949-954.

45. O'Keefe B R, Giomarelli B, Barnard D L, Shenoy S R, Chan P K S, McMahon J B, Palmer K E, Barnett B W, Meyerholz D K, Wohlford-Lenane C L, McCray P B Jr. Broad-Spectrum in Vitro Activity and in Vivo Efficacy of the Antiviral Protein Griffithsin Against Emerging Viruses of the Family Coronaviridae. *J Virol* 2010, p 2511-2521.

46. Wu J, Wang C, Liu Q, Yang T, Zhang Q, Peng J, Gao Y, Sun H, Kaku T, Liu K. Protective Effect of JBP485 on Concanavalin A-Induced Hepatocyte Toxicity in Primary Cultured Rat Hepatocytes. *Eur J Pharmacol* 2008, 589 (1-3), p 299-305.

47. Nadimpalli S K. Chemical Modification Studies on the Glucose/Mannose Specific Lectins from Field and *Lablab* Beans. *Biochem Mol Biol Int* 1999, 47(5), p 825-834.

48. Ekiert D C, Bhabha G, Elsliger M A, Friesen R H E, Jongeneelen M, Throsby M, Goudsmit J, Wilson I A. Antibody Recognition of a Highly Conserved Influenza Virus Epitope. *Science* 2009, 324, p 246-251.

49. WHO Global Influenza Surveillance Network. Manual for the Laboratory Diagnosis and Virological Surveillance of Influenza. Geneva: World Health Organization, 2011. Web.

50. Kase T, Suzuki Y, Kawai T, Sakamoto T, Ohtani K, Eda S, Maeda A, Okuno Y, Kurumura T, Wakamiya N. Human Mannan-Binding Lectin Inhibits the Infection of Influenza A Virus Without Complement. *Immunology* 1999, 97, p 385-392.

51. Balzarini J, Neyts J, Schols D, Hosoya M, Van Damme E, Peumans W, De Clercq E. The Mannose-Specific Plant Lectins from Cymbidium Hybrid and *Epipactis helleborine* and the (N-acetylglucosamine) N-Specific Plant Lectin from *Urtica dioica* are Potent and Selective Inhibitors of Human Immunodeficiency Virus and Cytomegalovirus Replication in Vitro. *Antiviral Res* 1992, 18(2), p 191-207.

52. Morimoto K, Sato Y. Anti-influenza Virus Activity of High-Mannose Binding Lectins Derived from Genus *Pseudomonas*. *Virus Res* 2016, 223, p 64-72.

53. Sato Y, Morimoto K, Hirayama M, Hori K. High Mannose-Specific Lectin (KAA-2) from the Red Alga *Kappaphycus alvarezii* Potently Inhibits Influenza Virus Infection in a Strain-Independent Manner. *Biochem Biophys Res Commun* 2011, 405(2), p 291-296.

54. Sato Y, Hirayama M, Morimoto K, Yamamoto N, Okuyama S, Hori K. High Mannose-Binding Lectin with Preference for the Cluster of Alpha1-2-Mannose from the Green Alga *Boodlea coacta* is a Potent Entry Inhibitor of HIV-1 and Influenza Viruses. *J Biol Chem* 2011, 286(22), p 19446-19458.

55. Ooi L S, Ho W S, Ngai K L, Tian L, Chan P K, Sun S S, Ooi V E. *Narcissus tazetta* Lectin Shows Strong Inhibitory Effects Against Respiratory Syncytial Virus, Influenza A (H1N1, H3N2, H5N1) and B Viruses. *J Biosci* 2010, 35(1), p 95-103.

56. Ooi L S, Sun S S, Ooi V E. Purification and Characterization of a New Antiviral Protein from the Leaves of *Pandanus amaryllifolius* (Pandanaceae). *Int J Biochem Cell Biol* 2004, 36(8), p 1440-1446.

57. Mu J, Hirayama M, Sato Y, Morimoto K, Hon K. A Novel High-Mannose Specific Lectin from the Green Alga *Halimeda renschii* Exhibits a Potent Anti-Influenza Virus Activity Through High-Affinity Binding to the Viral Hemagglutinin. *Mar Drugs* 2017, 15(8), E255.

58. Dalla Pellegrina C, Perbellini O, Scupoli M T, Tomelleri C, Zanetti C, Zoccatelli G, Fusi M, Peruffo A, Rizzi C, Chignola R. Effects of Wheat Germ Agglutinin on Human Gastrointestinal Epithelium: Insights from an Experimental Model of Immune/Epithelial Cell Interaction. *Toxicol Appl Pharmacol* 2009, 237(2), p 146-153.

59. Wetherall N T, Trivedi T, Zeller J, Hodges-Savola C, McKimm-Breschkin J L, Zambon M, Hayden F G. Evaluation of Neuraminidase Enzyme Assays Using Different Substrates to Measure Susceptibility of Influenza Virus Clinical Isolates to Neuraminidase Inhibitors: Report of the Neuraminidase Inhibitor Susceptibility Network. *J Clin Microbiol* 2003, 41(2), p 742-750.

60. *Corti* D, Voss J, Gamblin S J, Codoni G, Macagno A, Jarrossay D, Vachieri S G, Pinna D, Minola A, Vanzetta F, Silacci C, Fernandez-Rodriguez B M, Agatic G, Bianchi S, Giacchetto-Sasselli I, Calder L, Sallusto F, Collins P, Haire L F, Temperton N, Langedjik J P M, Skehel J J, Lanzavecchia A. A Neutralizing Antibody Selected from Plasma Cells That Binds to Group 1 and Group 2 Influenza A Hemagglutinins. *Science* 2011, 333, p 850-856.

61. Favero J, Corbean P, Nicolas M, Benkirame M, Truve G, Dixon J F P, Aucouturier P, Rashood S, Parker J W, Liautard J P, Devaux C, Dornand J. Inhibition of Human Immunodeficiency Virus Infection by the Lectin Jacalin and by a Derived Peptide Showing Sequence Similarity with Gp120. *Eur J Immunol* 1993, 23, p 179-185.

62. Wang L, Cummings R D, Smith D F, Huflejt M, Campbell C T, Gildersleeve J C, Gerlach J Q, Kilcoyne M, Joshi L, Serna S, Reichardt N C, Parera Pera N, Pieters R J, Eng W, Mahal L K. Cross-Platform Comparison of Glycan Microarray Formats. *Glycobiology* 2014, 24(6), p 507-517.

63. Min W, Dunn A J, Jones D H. Non-Glycosylated Recombinant Pro-Concanavalin A is Active Without Polypeptide Cleavage. *EMBO J* 1992, 11(4), p 1303-1307.

64. Tanaka I, Abe Y, Hamada T, Yonemitsu O, Ishii S. Monovalent Monomer Derivative of Concanavalin A Produced by Photochemically Induced Alkylation. *J Biochem* 1981, 89, p 1643-1646.

We claim:

1. A method for treating influenza virus infection comprising administering to a subject in need thereof an effective amount of a complex-type or hybrid-type glycan binding lectin or a composition comprising the same, wherein the lectin is an Flt3 receptor interacting lectin (FRIL) protein from *Lablab purpureous*.

2. The method of claim 1, wherein the lectin specifically binds to a complex -type or hybrid-type glycan which contains a trimannosyl core and at least one N -acetylglucosamine (GlcNAc) attached to the 1,3 mannose arm and/or the 1,6 mannose arm of the trimannosyl core and antenna residues.

3. The method of claim 2, wherein the glycan contains a α 1-3 and/or α 1-6 linked Manβ1-2GlcNacβ1-4 (Fucα1-3) Gal tetrasaccharide moiety.

4. The method of claim 1, wherein the lectin is in a form of a multimer.

5. The method of claim 1, wherein the lectin is administered in an amount effective in neutralizing multiple influenza virus strains.

6. The method of claim 5, wherein the FRIL protein comprises an amino acid sequence of SEQ ID No: 1, or an amino acid sequence that is at least 95% identical to SEQ ID NO: 1.

7. The method of claim 5, wherein the lectin is in a native form isolated from Lablab purpureous.

8. The method of claim 1, wherein the influenza virus infection is caused by an influenza A virus or an influenza B virus.

9. The method of claim 8, wherein the influenza A virus is HIN1, H5N1, H3N2, or H7N9 influenza virus.

10. The method of claim 1, wherein the subject is a human patient having the influenza virus infection.

11. The method of claim 1, wherein the lectin is administered after infection with the influenza virus.

12. A method for treating influenza virus infection comprising administering to a subject in need thereof an effective amount of an Flt3 receptor interacting lectin (FRIL) protein from Lablab purpureous or a composition comprising the same, wherein the influenza virus infection is caused by an influenza virus strain selected from the group consisting of A/California/7/2009, A/New Caledonia/20/1999, A/WSN/1933, A/Victoria/361/2011, A/Wisconsin/67/2005, A/Vietnam/1194/2004,A/Shanghai/02/2013, B/Brisbane/60/2008, B/Florida/4/2006, B/Malaysia/2506/2004 and any combination thereof.

13. The method of claim 12, wherein the influenza virus infection is caused by A/California/7/2009.

* * * * *

SEQUENCE LISTING

<160> NUMBER OF SEQ ID NOS: 5

<210> SEQ ID NO 1
<211> LENGTH: 272
<212> TYPE: PRT
<213> ORGANISM: Lablab purpureous

<400> SEQUENCE: 1

```
Met Phe Pro Ser Lys Val Lys Ser Ala Gln Ser Leu Ser Phe Ser Phe
1               5                   10                  15

Thr Lys Phe Asp Pro Asn Gln Glu Asp Leu Ile Phe Gln Gly His Ala
            20                  25                  30

Thr Ser Thr Asn Asn Val Leu Gln Val Thr Lys Leu Asp Ser Ala Gly
        35                  40                  45

Asn Pro Val Ser Ser Ser Ala Gly Arg Val Leu Tyr Ser Ala Pro Leu
    50                  55                  60

Arg Leu Trp Glu Asp Ser Ala Val Leu Thr Ser Phe Asp Thr Ile Ile
65                  70                  75                  80

Asn Phe Glu Ile Ser Thr Pro Tyr Thr Ser Arg Ile Ala Asp Gly Leu
                85                  90                  95

Ala Phe Phe Ile Ala Pro Pro Asp Ser Val Ile Ser Tyr His Gly Gly
            100                 105                 110

Phe Leu Gly Leu Phe Pro Asn Ala Asn Thr Leu Asn Asn Ser Ser Thr
            115                 120                 125

Ser Glu Asn Gln Thr Thr Thr Lys Ala Ala Ser Ser Asn Val Val Ala
    130                 135                 140

Val Glu Phe Asp Thr Tyr Leu Asn Pro Asp Tyr Gly Asp Pro Asn Tyr
145                 150                 155                 160

Ile His Ile Gly Ile Asp Val Asn Ser Ile Arg Ser Lys Val Thr Ala
                165                 170                 175

Lys Trp Asp Trp Gln Asn Gly Lys Ile Ala Thr Ala His Ile Ser Tyr
            180                 185                 190

Asn Ser Val Ser Lys Arg Leu Ser Val Thr Ser Tyr Tyr Ala Gly Ser
            195                 200                 205

Lys Pro Ala Thr Leu Ser Tyr Asp Ile Glu Leu His Thr Val Leu Pro
    210                 215                 220

Glu Trp Val Arg Val Gly Leu Ser Ala Ser Thr Gly Gln Asp Lys Glu
225                 230                 235                 240

Arg Asn Thr Val His Ser Trp Ser Phe Thr Ser Ser Leu Trp Thr Asn
            245                 250                 255

Val Ala Lys Lys Glu Asn Glu Asn Lys Tyr Ile Thr Arg Gly Val Leu
            260                 265                 270
```

<210> SEQ ID NO 2
<211> LENGTH: 113
<212> TYPE: PRT
<213> ORGANISM: Lablab purpureous

<400> SEQUENCE: 2

```
Ala Gln Ser Leu Ser Phe Ser Phe Thr Lys Phe Asp Pro Asn Gln Glu
1               5                   10                  15

Asp Leu Ile Phe Gln Gly His Ala Thr Ser Thr Asn Asn Val Leu Gln
            20                  25                  30

Val Thr Lys Leu Asp Ser Ala Gly Asn Pro Val Ser Ser Ser Ala Gly
        35                  40                  45

Arg Val Leu Tyr Ser Ala Pro Leu Arg Leu Trp Glu Asp Ser Ala Val
```

```
                                 -continued 50              55              60

Leu Thr Ser Phe Asp Thr Ile Ile Asn Phe Glu Ile Ser Thr Pro Tyr
65                  70              75                  80

Thr Ser Arg Ile Ala Asp Gly Leu Ala Phe Phe Ile Ala Pro Pro Asp
                85              90              95

Ser Val Ile Ser Tyr His Gly Gly Phe Leu Gly Leu Phe Pro Asn Ala
                100             105             110

Asn

<210> SEQ ID NO 3
<211> LENGTH: 17
<212> TYPE: PRT
<213> ORGANISM: Lablab purpureous

<400> SEQUENCE: 3

Thr Leu Asn Asn Ser Ser Thr Ser Glu Asn Gln Thr Thr Thr Lys Ala
1               5               10              15

Ala

<210> SEQ ID NO 4
<211> LENGTH: 134
<212> TYPE: PRT
<213> ORGANISM: Lablab purpureous

<400> SEQUENCE: 4

Ser Ser Asn Val Val Ala Val Glu Phe Asp Thr Tyr Leu Asn Pro Asp
1               5               10              15

Tyr Gly Asp Pro Asn Tyr Ile His Ile Gly Ile Asp Val Asn Ser Ile
                20              25              30

Arg Ser Lys Val Thr Ala Lys Trp Asp Trp Gln Asn Gly Lys Ile Ala
                35              40              45

Thr Ala His Ile Ser Tyr Asn Ser Val Ser Lys Arg Leu Ser Val Thr
        50              55              60

Ser Tyr Tyr Ala Gly Ser Lys Pro Ala Thr Leu Ser Tyr Asp Ile Glu
65              70              75              80

Leu His Thr Val Leu Pro Glu Trp Val Arg Val Gly Leu Ser Ala Ser
                85              90              95

Thr Gly Gln Asp Lys Glu Arg Asn Thr Val His Ser Trp Ser Phe Thr
                100             105             110

Ser Ser Leu Trp Thr Asn Val Ala Lys Lys Glu Asn Glu Asn Lys Tyr
        115             120             125

Ile Thr Arg Gly Val Leu
        130

<210> SEQ ID NO 5
<211> LENGTH: 8
<212> TYPE: PRT
<213> ORGANISM: Lablab purpureous

<400> SEQUENCE: 5

Met Phe Pro Ser Lys Val Lys Ser
1               5
```